United States Patent [19]
Horwell et al.

[11] Patent Number: 6,057,357
[45] Date of Patent: May 2, 2000

[54] PERIPHERALLY SELECTIVE KAPPA OPIOID AGONISTS

[75] Inventors: David Christopher Horwell, Cambridge; Simon Osborne, Suffolk, both of United Kingdom

[73] Assignee: Warner-Lambert Company, Morris Plains, N.J.

[21] Appl. No.: 09/331,753

[22] PCT Filed: Apr. 2, 1998

[86] PCT No.: PCT/US98/06485

§ 371 Date: Jun. 24, 1999

§ 102(e) Date: Jun. 24, 1999

[87] PCT Pub. No.: WO98/49158

PCT Pub. Date: Nov. 5, 1998

Related U.S. Application Data

[60] Provisional application No. 60/046,986, Apr. 30, 1997, and provisional application No. 60/074,547, Feb. 12, 1998.

[51] Int. Cl.[7] .......................... A01N 43/36; C07D 405/12
[52] U.S. Cl. ............................................. 514/422; 548/525
[58] Field of Search ............................ 548/525; 514/422

[56] References Cited

U.S. PATENT DOCUMENTS 4,737,493  4/1988  Horwell .................................. 514/212
5,229,414  7/1993  Main ....................................... 514/428

FOREIGN PATENT DOCUMENTS 0254545  1/1988  European Pat. Off. .

*Primary Examiner*—Johann Richter
*Assistant Examiner*—Dominic Keating
*Attorney, Agent, or Firm*—Elizabeth A. Anderson

[57] ABSTRACT

The compounds of the instant invention as those of Formula I

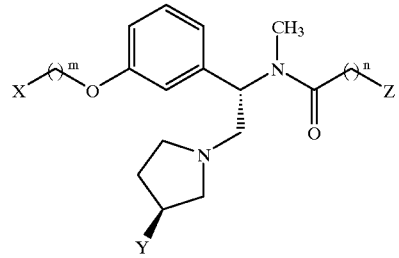

or a pharmaceutically acceptable salt thereof are peripherally selective kappa opioid agonists that are useful in treating pain, inflammation, psoriasis and irritable bowel syndrome.

14 Claims, No Drawings

PERIPHERALLY SELECTIVE KAPPA OPIOID AGONISTS

This application is a 371 of PCT/US98/06485, filed Apr. 2, 1998, which claims the priority benefit of U.S. Provisional Applications Nos. 60/046,980, filed Apr. 30, 1997 and 60/074,547, filed Feb. 12, 1998.

BACKGROUND OF THE INVENTION

The compounds of the instant invention are polar compounds designed to have a low log D and thereby have a limited ability to cross the blood-brain barrier. This means that the side effects associated with centrally acting kappa opioid agonists are greatly reduced upon administration of these compounds to a mammal, preferably a human, in need of treatment. Such side effects are various CNS problems and dysphoria.

The compounds of the instant invention are compared to [5R-(5α,7α,8β)]-N-methyl-N-[7-(1-pyrrolidinyl)-1-oxaspiro-[4,5]dec-8-yl]-4-benzofuranacetamide, monohydrochloride, which is described and claimed in U.S. Pat. No. 4,737,493 which patent is hereby incorporated by reference.

SUMMARY OF THE INVENTION

The compounds of the instant invention as those of Formula I

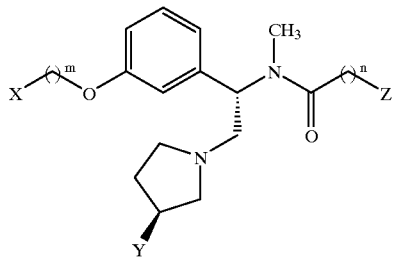

I or a pharmaceutically acceptable salt thereof wherein X, m, Y, n, and Z are as described below.

Preferred compounds of the invention are those of Formula I wherein Z is 2-benzofuranyl, 3-benzofuranyl, 4-benzofuranyl, 5-benzofuranyl, 6-benzofuranyl, 7-benzofuranyl, 4-(methylsulphonyl)phenyl, 3-(methylsulphonyl)phenyl, 2-thianaphthene, 3-thianaphthene, 4-thianaphthene, 5-thianaphthene, 6-thianaphthene, or 7-thianaphthene, and n is 1.

Other preferred compounds are those of Formula I wherein Z is diphenylcyclopropene or diphenylmethyl, and n is zero.

More preferred compounds are those selected from:
(S)-(3-{1-[(Benzofuran-2-yl-acetyl)-methyl-amino]-2-pyrrolidin-1-yl-ethyl}-phenoxy)-acetic acid;
(S)-(3-{1-[(Benzofuran-3-yl-acetyl)-methyl-amino]-2-pyrrolidin-1-yl-ethyl}-phenoxy)-acetic acid;
[S-(R*,R*)]-{3-[1-[(Benzofuran-3-yl-acetyl)-methyl-amino]-2-(3-hydroxy-pyrrolidin-1-yl)-ethyl]-phenoxy}-acetic acid;
[S-(R*,R*)]-{3-[1-[(Benzofuran-2-yl-acetyl)-methyl-amino]-2-(3-hydroxy-pyrrolidin-1-yl)-ethyl]-phenoxy}-acetic acid; and
[S-(R*,R*)]-{3-[1-[(Benzofuran-4-yl-acetyl)-methyl-amino]-2-(3-hydroxy-cyclopentyl)-ethyl]-phenoxy}-acetic acid.

Other preferred compounds are:
(S)-(3-{1-[(Thianaphthen-2-yl-acetyl)-methyl-amino]-2-pyrrolidin-1-yl-ethyl}-phenoxy)-acetic acid;
(S)-2-Benzofuran-2-yl-N-methyl-N-{2-pyrrolidin-1-yl-1-[3-(2H-tetrazol-5-ylmethoxy)-phenyl]-ethyl}-acetamide;
[S-(R*,R*)]-{3-[1-[(Benzofuran-4-yl-acetyl)-methyl-amino]-2-(3-fluoropyrrolidin-1-yl)-ethyl]-phenoxy}-acetic acid;
(S)-(3-{1-[(Benzofuran-2-yl-acetyl)-methyl-amino]-2-pyrrolidin-1-yl-ethyl}-phenoxy)-methanesulfonic acid;
[S-(R*,R*)]-{3-[1-[(Benzofuran-4-yl-acetyl)-methyl-amino]-2-(3-methoxy-pyrrolidin-1-yl)-ethyl]-phenoxy}-acetic acid;

Other more preferred compounds are those selected from:
(S)-[3-(1-{[(4-Methanesulfonyl-phenyl)-acetyl]-methyl-amino}-2-pyrrolidin-1-yl-ethyl)-phenoxy]-acetic acid tert-butyl ester,
[S-(R*,R*)]-[3-(2-(3-Hydroxy-cyclopentyl)-1-{[(4-methanesulfonyl-phenyl)-acetyl]-methyl-amino}-ethyl)-phenoxy]-acetic acid,
(S)-(3-{1-[(Thianaphthen-2-yl-acetyl)-methyl-amino]-2-pyrrolidin-1-yl-ethyl}-phenoxy)-acetic acid,
(S)-2-Benzofuran-2-yl-N-methyl-N-{2-pyrrolidin-1-yl-1-[3-(2H-tetrazol-5-ylmethoxy)-phenyl]-ethyl}-acetamide,
[S-(R*,R*)]-{3-[1-[(Benzofuran-4-yl-acetyl)-methyl-amino]-2-(3-fluoro-pyrrolidin-1-yl)-ethyl]-phenoxy}-acetic acid,
(S)-(3-{1-[(Benzofuran-2-yl-acetyl)-methyl-amino]-2-pyrrolidin-1-yl-ethyl}-phenoxy)-methanesulfonic acid, and
[S-(R*,R*)]-{3-[1-[(Benzofuran-4-yl-acetyl)-methyl-amino]-2-(3-methoxy-pyrlrolidin-1-yl)-ethyl]-phenoxy}-acetic acid.

Other compounds are:
[S-(R*,R*)]-{3-[1-[(Benzofuran-4-yl-acetyl)-methyl-amino]-2-(3-fluoro-pyrrolidin-1-yl)-ethyl]-phenoxy}-acetic acid,
[S-(R* ,R*)]-{3-[1-[(Benzofuran-4-yl-acetyl)-methyl-amino]-2-(3-methoxy-pyrlrolidin-1-yl)-ethyl]-phenoxy}-acetic acid,
[S-(R*,R*)]-2-Benzofuran-4-yl-N-{2-(3-hydroxy-pyrrolidin-1-yl)-1-[3-(2H-tetrazol-5-ylmethoxy)-phenyl]-ethyl}-N-methyl-acetamide,
[S-(R*,R*)]-{3-[1-[(Benzofuran-4-yl-acetyl)-methyl-amino]-2-(3-hydroxy-pyrrolidin-1-yl)-ethyl]-phenoxy}-methanesulfonic acid,
[S-(R*,R*)]-2-Benzofuran-4-yl-N-{2-(3-fluoro-pyrrolidin-1-yl)-1-[3-(2H-tetrazol-5-ylmethoxy)-phenyl]-ethyl}-N-methyl-acetamide,
[S-(R*,R*)]-2-Benzofuran-4-yl-N-{2-(3-methoxy-pyrrolidin-1-yl)-1-[3-(2H-tetrazol-5-ylmethoxy)-phenyl]-ethyl}-N-methyl-acetamide,
[S-(R*,R*)]-{3-[1-[(Benzofuran-2-yl-acetyl)-methyl-amino]-2-(3-fluoro-pyrrolidin-1-yl)-ethyl]-phenoxy}-acetic acid,
[S-(R*,R*)]-{3-[1-[(Benzofuran-2-yl-acetyl)-methyl-amino]-2-(3-methoxy-pyrrolidin-1-yl)-ethyl]-phenoxy}-acetic acid,
[S-(R*,R*)-2-Benzofuran-2-yl-N-{2-(3-hydroxy-pyrrolidin-1-yl)-1-[3-(2H-tetrazol-5-ylmethoxy)-phenyl]-ethyl}-N-methyl-acetamide,
[S-(R*,R*)]-2-Benzofuran-2-yl-N-{2-(3-fluoro-pyrrolidin-1-yl)-1-[3-(2H-tetrazol-5-ylmethoxy)-phenyl]-ethyl}-N-methyl -acetamide,
[S-(R*,R*)]-2-Benzofuran-2-yl-N-{2-(3-methoxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-2-yl-acetyl)-methyl-amino]-2-(3-hydroxy-pyrrolidin-1-yl)-ethyl]-phenoxy}-methanesulfonic acid, (S)-2-Benzofuran-2-yl-N-methyl-N-{2-pyrrolidin-1-yl-1-[3-(2H-tetrazol-5-ylmethoxy)-phenyl]-ethyl}-acetamide, (S)-(3-{1-[(Benzofuran-2-yl-acetyl)-methyl-amino]-2-pyrrolidin-1-yl-ethyl}-phenoxy)-methanesulfonic acid,

[S-(R*,R*)]-{3-[1-(Diphenylacetyl-methyl-amino)-2-(3-fluoro-pyrrolidin-1-yl)-ethyl]-phenoxy}-acetic acid,

[S-(R*,R*)]-{3-[1-(Diphenylacetyl-methyl-amino)-2-(3-methoxy-pyrrolidin-1-yl)-ethyl]-phenoxy}-acetic acid,

[S-(R*,R*)]-N-{2-(3-Hydroxy-pyrrolidin-1-yl)-1-[3-(2H-tetrazol-5-ylmethoxy)-phenyl]-ethyl}-N-methyl-2,2-diphenyl-acetamide,

[S-(R*,R*)]-{3-[1-(Diphenylacetyl-methyl-amino)-2-(3-hydroxy-pyrrolidin-1-yl)-ethyl]-phenoxy}-methanesulfonic acid,

[S-(R*,R*)]-N-{2-(3-Fluoro-pyrrolidin-1-yl)-1-[3-(2H-tetrazol-5-ylmethoxy)-phenyl]-ethyl}-N-methyl-2,2-diphenyl-acetamide,

[S-(R*,R*)]-N-{2-(3-Methoxy-pyrrolidin-1-yl)-1-[3-(2H-tetrazol-5-ylmethoxy)-phenyl]-ethyl}-N-methyl-2,2-diphenyl-acetamide,

[S-(R*,R*)]-[3-(2-(3-Fluoro-pyrrolidin-1-yl)-1-{[(4-methanesulfonyl-phenyl)-acetyl]-methyl-amino}-ethyl)-phenoxy]-acetic acid,

[S-(R*,R*)]-{3-[1-{[(4-Methanesulfonyl-phenyl)-acetyl]-methyl-amino}-2-(3-methoxy-pyrrolidin-1-yl)-ethyl]-phenoxy}-acetic acid,

[S-(R*,R*)]-N-{2-(3-Hydroxy-pyrrolidin-1-yl)-1-[3-(2H-tetrazol-5-ylmethoxy)-phenyl]-ethyl}-2-(4-methanesulfonyl-phenyl)-N-methyl-acetamide,

[S-(R*,R*)]-[3-(2-(3-Hydroxy-pyrrolidin-1-yl)-1-{[(4-methanesulfonyl-phenyl)-acetyl]-methyl-amino}-ethyl)-phenoxy]-methanesulfonic acid,

[S-(R*,R*)]-N-{2-(3-Fluoro-pyrrolidin-1-yl)-]-[3-(2H-tetrazol-5-ylmethoxy)-phenyl]-ethyl}-2-(4-methanesulfonyl-phenyl)-N-methyl-acetamide,

[S-(R*,R*)]-2-(4-Methanesulfonyl-phenyl)-N-{2-(3-methoxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-3-yl-acetyl)-methyl-amino]-2-(3-fluoro-pyrrolidin-1-yl)-ethyl]-phenoxy}-acetic acid,

[S-(R*,R*)]-{3-[1-[(Benzofuran-3-yl-acetyl)-methyl-amino]-2-(3-methoxy-pyrrolidin-1-yl)-ethyl]-phenoxy}-acetic acid,

[S-(R*,R*)]-2-Benzofuran-3-yl-N-{2-(3-hydroxy-pyrrolidin-1-yl)-1-1-[3-(2H-tetrazol-5-ylmethoxy)-phenyl]-ethyl}-N-methyl-acetamide,

[S-(R*,R*)]-2-Benzofuran-3-yl-N-{2-(3-fluoro-pyrrolidin-1-yl)-1-[3-(2H-tetrazol-5-ylmethoxy)-phenyl]-ethyl}-N-methyl-acetamide,

[S-(R*,R*)]-2-Benzofuran-3-yl-N-{2-(3-methoxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-3-yl-acetyl)-methyl-amino]-2-(3-hydroxy-pyrrolidin-1-yl)-ethyl]-phenoxy}-methanesulfonic acid, (S)-2-Benzofuran-3-yl-N-methyl-N-{2-pyrrolidin-1-yl-1-[3-(2H-tetrazol-5-ylmethoxy)-phenyl]-ethyl}-acetamide, and (S)-(3-{1-[(Benzofuran-3-yl-acetyl)-methyl-amino]-2-pyrrolidin-1-yl-ethyl}-phenoxy)-methanesulfonic acid.

A pharmaceutical composition comprising a compound of Formula I in a therapeutically effective amount in combination with a pharmaceutically acceptable carrier in unit dosage form is another aspect of the instant invention.

The compounds of the invention are useful in the treatment of pain, inflammation, migraine, inflammatory disorders of the gastrointestinal tract, psoriasis, and irritable bowel syndrome (IBS).

Processes for the preparation of novel compounds are yet another aspect of the invention. The novel intermediates are still another aspect of the invention. They are:

(S)-[1-(3-Benzyloxy-phenyl)-2-pyrrolidin-1-yl-ethyl]-methyl-amine,

[S-(R*,R*)]-{1-(3-Benzyloxy-phenyl)-2-[3-(tert-butyl-dimethyl-silanyloxy)-pyrrolidin-1-yl]-ethyl}-methyl-amine, (S)-2-Benzofuran-2-yl-N-[1-(3-benzyloxy-phenyl)-2-pyrrolidin-1-yl-ethyl]-N-methyl-acetamide, (S)-2-Benzofuran-2-yl-N-[1-(3-hydroxy-phenyl)-2-pyrrolidin-1-yl-ethyl]-N-methyl-acetamide, (S)-2-Benzofuran-2-yl-N-[1-(3-hydroxy-phenyl)-2-pyrrolidin-1-yl-ethyl]-N-methyl-acetamide, (S)-2-Benzofuran-3-yl-N-[1-(3-benzyloxy-phenyl)-2-pyrrolidin-1-yl-ethyl]-N-methyl-acetamide, (S)-2-Benzofuran-3-yl-N-[1-(3-hydroxy-phenyl)-2-pyrrolidin-1-yl-ethyl]-N-methyl-acetamide, (S)-(3-{1-[(Benzofuran-3-yl-acetyl)-methyl-amino]-2-pyrrolidin-1-yl-ethyl}-phenoxy)-acetic acid tert-butyl ester, (S)-N-[1-(3-Benzyloxy-phenyl)-2-pyrrolidin-1-yl-ethyl]-2-(4-methanesulfonyl-phenyl)-N-methyl-acetamide, (S)-N-[1-(3-Hydroxy-phenyl)-2-pyrrolidin-1-yl-ethyl]-2-(4-methanesulfonyl-phenyl)-N-methyl-acetamide, (S)-[3-(1-{[(4-Methanesulfonyl-phenyl)-acetyl]-methyl-amino}-2-pyrrolidin-1-yl-ethyl)-phenoxy]-acetic acid tert-butyl ester,

[S-(R*,R*)]-2-Benzofuran-3-yl-N-{1-(3-benzyloxy-phenyl)-2-[3-(tert-butyl-dimethyl-silanyloxy)-pyrrolidin-1-yl]-ethyl}-N-methyl-acetamide,

[S-(R*,R*)]-2-Benzofuran-3-yl-N-[2-[3-(tert-butyl-dimethyl-silanyloxy)-pyrrolidin-1-yl]-1-(3-hydroxy-phenyl)-ethyl]-N-methyl-acetamide,

[S-(R*,R*)]-(3-{1-[(Benzofuran-3-yl-acetyl)-methyl-amino]-2-[3-(tert-butyl-dimethyl-silanyloxy)-pyrrolidin-1-yl -ethyl}-phenoxy)-acetic acid tert-butyl ester,

[S-(R*,R*)]-{3-[1-[(Benzofuran-3-yl-acetyl)-methyl-amino]-2-(3-hydroxy-pyrrolidin-1-yl)-ethyl]-phenoxy}-acetic acid tert-butyl ester,

[S-(R*,R*)]-2-Benzofuran-2-yl-N-{1-(3-benzyloxy-phenyl)-2-[3-(tert-butyl-dimethyl-silanyloxy)-pyrrolidin-1-yl]-ethyl}-N-methyl-acetamide,

[S-(R*,R*)]-2-Benzofuran-2-yl-N-[2-[3-(tert-butyl-dimethyl-silanyloxy)-pyrrolidin-1-yl]-1-(3-hydroxy-phenyl)-ethyl]-N-methyl-acetamide,

[S-(R*,R*)]-(3-{1-[(Benzofuran-2-yl-acetyl)-methyl-amino]-2-[3-(tert-butyl-dimethyl-silanyloxy)-pyrrolidin-1-yl]-ethyl}-phenoxy)-acetic acid tert-butyl ester,

[S-(R*,R*)]-{3-[1-[(Benzofuran-2-yl-acetyl)-methyl-amino]-2-(3-hydroxy-pyrrolidin-1-yl)-ethyl]-phenoxy}-acetic acid tert-butyl ester,

[S-(R*,R*)]-2-Benzofuran-4-yl-N-{1-(3-benzyloxy-phenyl)-2-[3-(tert-butyl-dimethyl-silanyloxy)-2-pyrrolidin-1-yl]-ethyl}-N-methyl-acetamide,

[S-(R*,R*)-2-Benzofuran-4-yl-N-[2-[3-(tert-butyl-dimethyl-silanyloxy)-cyclopentyl]-1-(3-hydroxy-phenyl)-ethyl]-N-methyl-acetamide,

[S-(R*,R*)]-(3-{1-[(Benzofuran-4-yl-acetyl)-methyl-amino]-2-[3-(tert-butyl-dimethyl-silanyloxy)-cyclopentyl]-ethyl}-phenoxy)-acetic acid tert-butyl ester,

[S-(R*,R*)]-{3-[1-[(Benzofuran-4-yl-acetyl)-methyl-amino]-2-(3-hydroxy-cyclopentyl)-ethyl]-phenoxy}-acetic acid tert-butyl ester,

[S-(R*,R*)]-N-{1-(3-Benzyloxy-phenyl)-2-[3-(tert-butyl-dimethyl-silanyloxy)-cyclopentyl]-ethyl}-2-(4-methanesulfonyl-phenyl)-N-methyl-acetamide,

[S-(R*,R*)]-N-[2-[3-(tert-Butyl-dimethyl-silanyloxy)-cyclopentyl]-1-(3-hydroxy-phenyl)-ethyl]-2-(4-methanesulfonyl-phenyl)-N-methyl-acetamide,

[S-(R*,R*)]-[3-(2-[3-(tert-Butyl-dimethyl-silanyloxy)-cyclopentyl]-{[(4-methanesulfonyl-phenyl)-acetyl]-methyl-amino}-ethyl)-phenoxy]-acetic acid tert-butyl ester, and

[S-(R*,R*)]-[3-(2-(3-Hydroxy-cyclopentyl)-1-{[(4-methanesulfonyl-phenyl)-acetyl]-methyl-amino}-ethyl)-phenoxy]-acetic acid tert-butyl ester.

DETAILED DESCRIPTION OF THE INVENTION

The compounds covered below are selective kappa opioid agonists. They are polar compounds designed to have a low log D and hence a limited ability to cross the blood-brain barrier. The side effects associated with centrally acting kappa agonists are thus reduced. This reduction in side effects is of great value in the treatments provided in this invention.

The compounds of the instant invention are those of Formula I above wherein:

X=$CO_2H$, $SO_3H$, or tetrazole;

m is an integer of from 1 to 3;

Y is hydrogen, fluoro, or OR wherein R is hydrogen or methyl;

n is an integer of from 0 to 1; and

Z is 2-benzofuranyl, 3-benzofuranyl, 4-benzofuranyl, 5-benzofuranyl, 6-benzofuranyl, 7-benzofuranyl, 4-(methylsulphonyl)phenyl, 3-(methylsulphonyl)phenyl, 2-thianaphthene, 3-thianaphthene, 4-thianaphthene, 5-thianaphthene, 6-thianaphthene, or 7-thianaphthene when n is 1 and Z is diphenylcyclopropene or diphenylmethyl when n is 0.

Compounds of the present invention contain one or more asymmetric carbon atoms and therefore exist in various stereoisomeric forms. Additionally, the compounds of this invention exist in different geometric isomeric forms. The instant invention is all geometric and stereoisomeric forms.

The compounds of the present invention and/or their nontoxic, pharmaceutically acceptable acid addition salts may be administered to mammals in pharmaceutical compositions which comprise one or more compounds of this invention and/or salts thereof in combination with a pharmaceutically acceptable nontoxic carrier.

As parenteral compositions, the compounds of this invention may be administered with conventional injectable liquid carriers such as sterile, pyrogen-free water, sterile peroxide-free ethyl oleate, dehydrated alcohols, polypropylene glycol, and mixtures thereof.

Suitable pharmaceutical adjuvants for the injectable solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously.

As solid or liquid pharmaceutical compositions, the compounds of the present invention may be administered to mammals orally in combination with conventional compatible carriers in solid or liquid form. These orally administered pharmaceutical compositions may contain conventional ingredients such as binding agents such as syrups, acacia, gelatin, sorbitol, tragacanth, polyvinylpyrrolidone, and mixtures thereof.

The compositions may further include fillers such as lactose, mannitol, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The oral pharmaceutical compositions may take any convenient form such as tablets, capsules, lozenges, aqueous or oily suspensions, emulsions, or even dry powders which may be reconstituted with water or other suitable liquids prior to use.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may be encapsulated in, for example, gelatin capsules.

As topically administered pharmaceutical compositions, the compounds of the present invention may be administered in the form of ointments or creams containing from about 0.1% to about 10% by weight of the active component in a pharmaceutical ointment or cream base.

Compounds of the present invention may be rectally administered in the form of suppositories. For preparing suppositories, a low-melting wax such as a mixture of fatty acid glycerides or cocoa butter is first melted, and the active ingredient is dispersed homogeneously in the melt. The mixture is then poured into convenient-sized molds and allowed to cool and solidify.

Preferably, the pharmaceutical compositions of this invention are in unit dosage form. In such form, the preparation is subdivided into unit doses containing appropriate amounts of the active component. The unit dosage can be a packaged preparation with the package containing discrete quantities of the preparation. For example, the package may take the form of packaged tablets, capsules, and powders in envelopes, vials, or ampoules. The unit dosage form can also be a capsule, cachet, or tablet itself or can be the appropriate number of any of these packaged forms.

The quantity of active compound in the unit dosage form may be varied or adjusted from about 0.5 mg to about 350 mg according to the particular application and the potency of the active ingredient.

When employed systematically in therapeutic use as analgesic agents in the pharmaceutical method of this invention, the compounds are administered at doses of from about 0.05 mg to about 2.0 mg of active compound per kilogram of body weight of the recepient.

The rabbit vas deferens is a specific test for activity at the K-receptor and allows comparison of potency and efficacy of a test ligand and its parent K-agonist. Rabbit vas deferens assay (Oka T., Negiski K et al., *Eur. J. Pharmacol.*, 1981;73:235) was used to test the compounds of the invention.

The potency of the compounds listed below is the $EC_{50}$ compared to the $EC_{50}$ of [5R-(5α,7α,8β)]-N-methyl-N-[7-(1-pyrrolidinyl)-1-oxaspiro-[4.5]dec-8-yl]-4-benzofuranacetamide, monohydrochloride.

TABLE 1

| Compound | Potencies |
|---|---|
| 15 | 5.3 |
| 19 | 5.8 |
| 23 | 30.2 |
| 28 | 0.62 |
| 33 | 0.62 |
| 38 | 0.66 |
| 43 | 0.66 |

The results of the testing shown in Table 1 above show that the compounds of the invention are kappa opioid agonists and thus are useful in the treatment of arthritis, hypertension, pain (particularly pain which is inflammatory in origin and post-operative pain), inflammation, migraine, and inflammatory disorders of the gastrointestinal tract, IBS, and psoriasis.

The data in Table 2 below show that the compounds of the invention are analgesics and are peripherally selective.

TABLE 2

| Compound Number | Mouse Formalin Test $ED_{50}$ (mg/kg) | Mouse Rotarod $ED_{50}$ (mg/kg) |
|---|---|---|
| 23 | 6.1 | |
| 15 | 2.95 | >>10 (0%) |
| 38 | 0.95 | >>10 (0%) |
| 43 | 0.51 | >>10 (0%) |
| 28 | 0.36 | =10 (53%) |
| 33 | 0.19 | =10 (53%) |
| 19 | 1.17 | >>10 (0%) |

The formalin test and the rotarod test are outlined below:

Formalin Test in Mice: Late Phase

Swiss male mice (IFFA-CREDO) at 22±3 grams on test day.

Room temperature: 24.5<T<24.8° C.

Procedure:

t=−10 minutes. Subcutaneous administration of drug at 1 mL/100 g body weight. Either as a solution in distilled water or suspension in an aqueous solution of hydroxypropylmethylcellulose 0.2% (v/v).

t=0 minutes. Formalin 5% in sterile saline (v/v) administered by intraplanatar injection (20 µL) into the left paw.

t=+15 minutes. Mouse placed in cylinder.

t=+25 minutes. Nociceptive reaction: number of times left paw is licked during the observation period.

Results: Mean±sem per group

Dunnett's test after analysis of variance (Anova one way).

Reference: S. Hunskaar, *Journal of Neuroscience Methods*, 1985;14:69–76.

Rotarod Test in Mice

Swiss male mice (IFFA-CREDO) at 22±3 grams on the test day.

Room temperature: 21.2±0.2° C.

Rotarod (Ugobasile) at 18 rotations per minute.

Procedure:

t=−180 minutes and t=−120 minutes: mice trained to stay on the bar at least 120 seconds before falling off.

t=−30 minutes: Subcutaneous administration of drug at 1 mL/100 g body weight as either solution in distilled water or suspension in an aqueous solution of hydroxypropylmethylcellulose 0.2% (v/v).

t=0 minutes: Ataxic reaction: time taken for mouse to fall off the rotarod (maximum time 120 seconds).

Results: Mean±sem per group

Dunnett's test after analysis of variance (Anova one way).

The following Schemes describe the preparation of intermediates and final products of the instant invention. The numbers correspond to the numbered examples below.

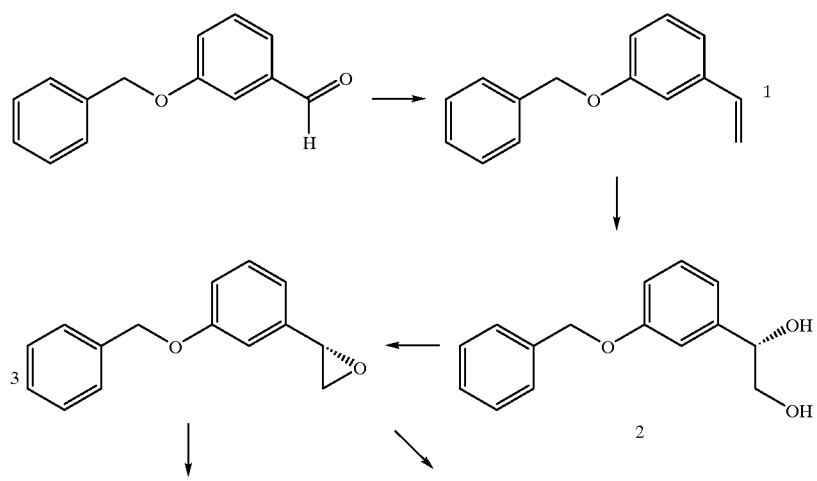

Scheme 1

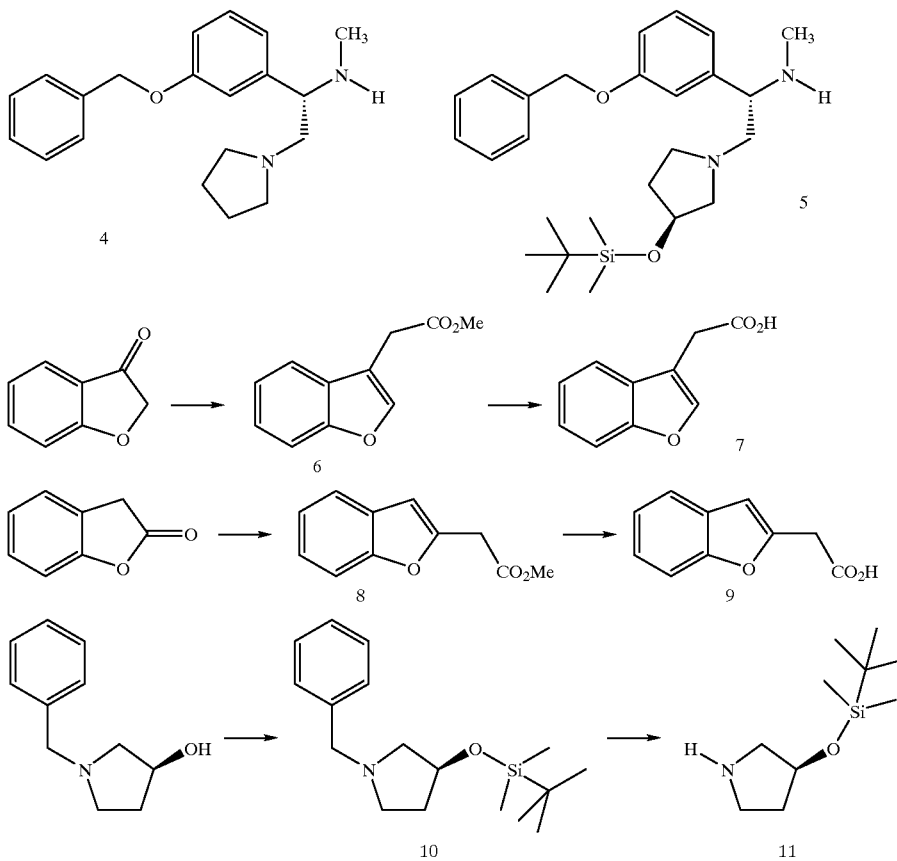
For synthesis of compounds 6, 7, 8, and 9: Elix et al., *Synthetic Communications*, 1972;2(6):409–414.
For synthesis of 2 from 1: Sharpless et al. *Chemical Reviews*, 1994;94:2483–2547.
For conversion of 2 into 3: Sharpless et al., *Tetrahedron*, 1992;48:10515–10530.
For synthesis of 4 and 5 from 3: O'Brien et al., *Tetrahedron Lett.*, 1996;37:5619–5622.
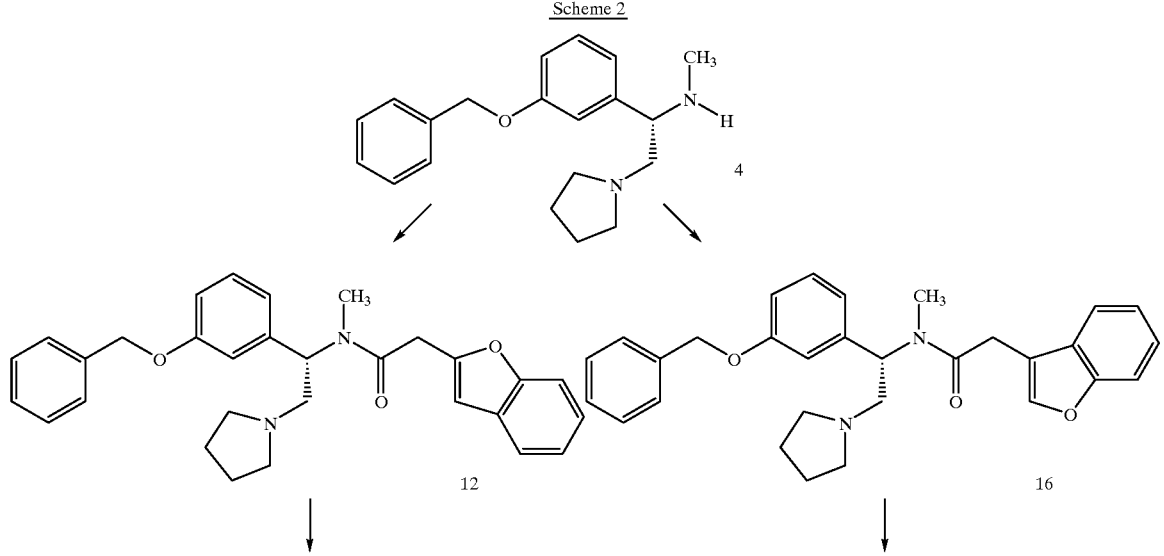

11 12
-continued
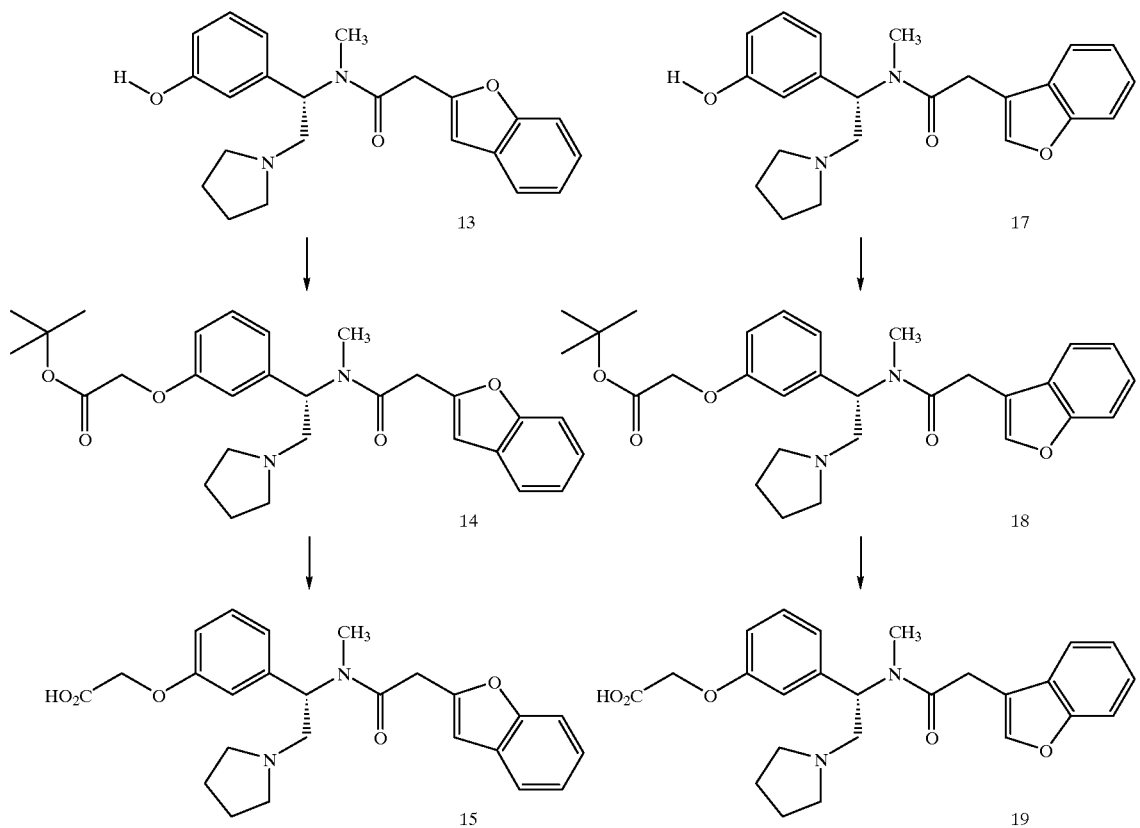
Scheme 3
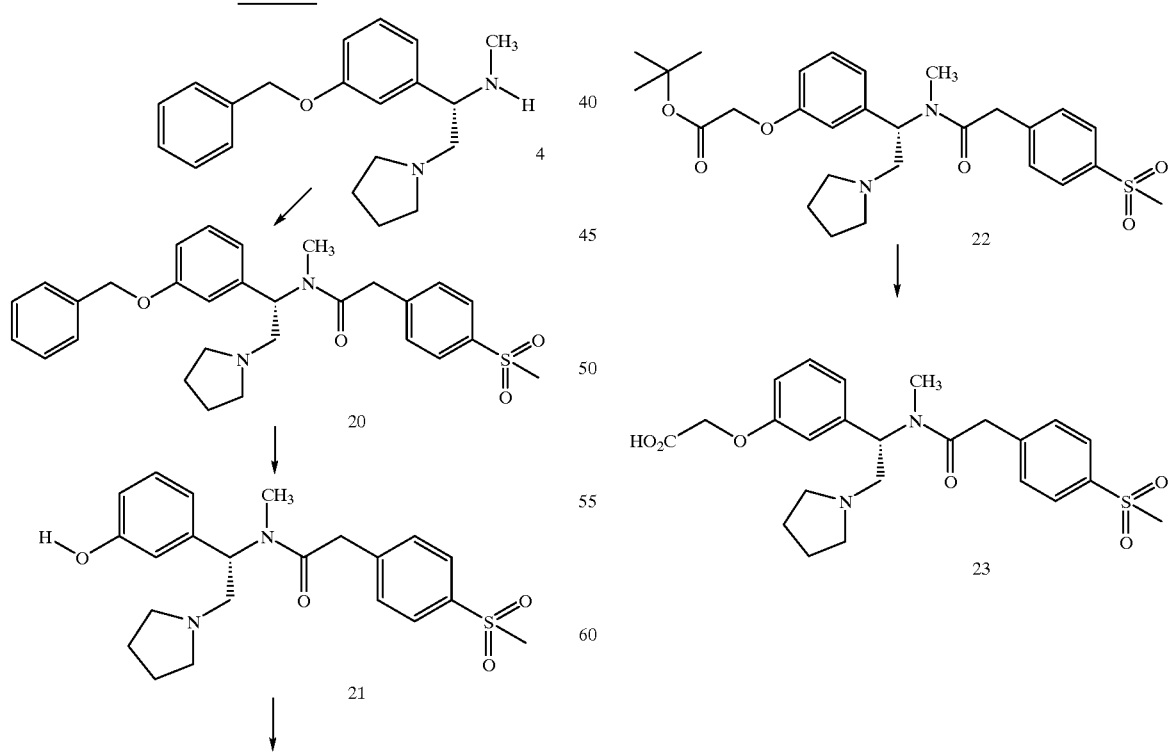

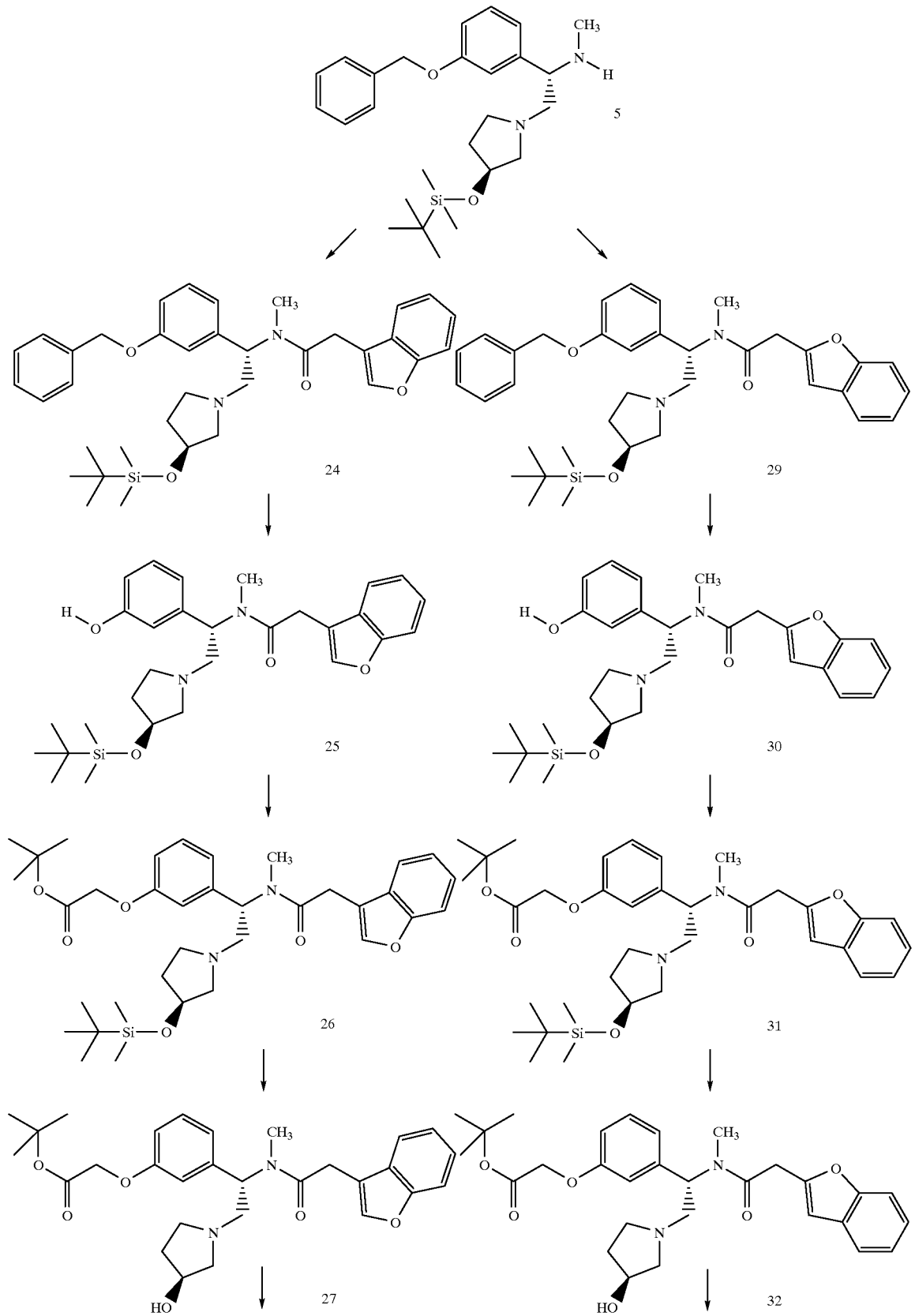
Scheme 4

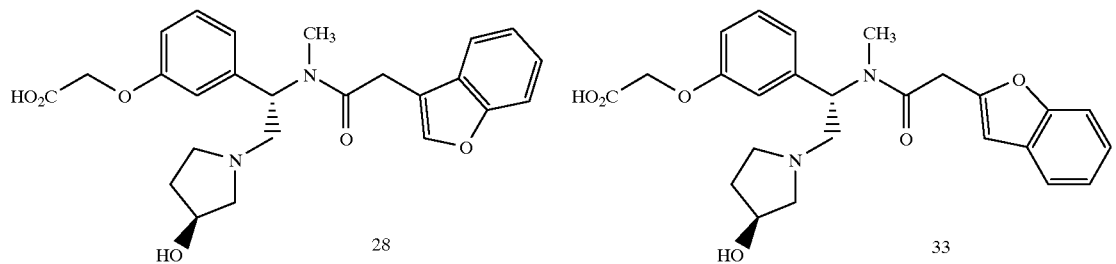
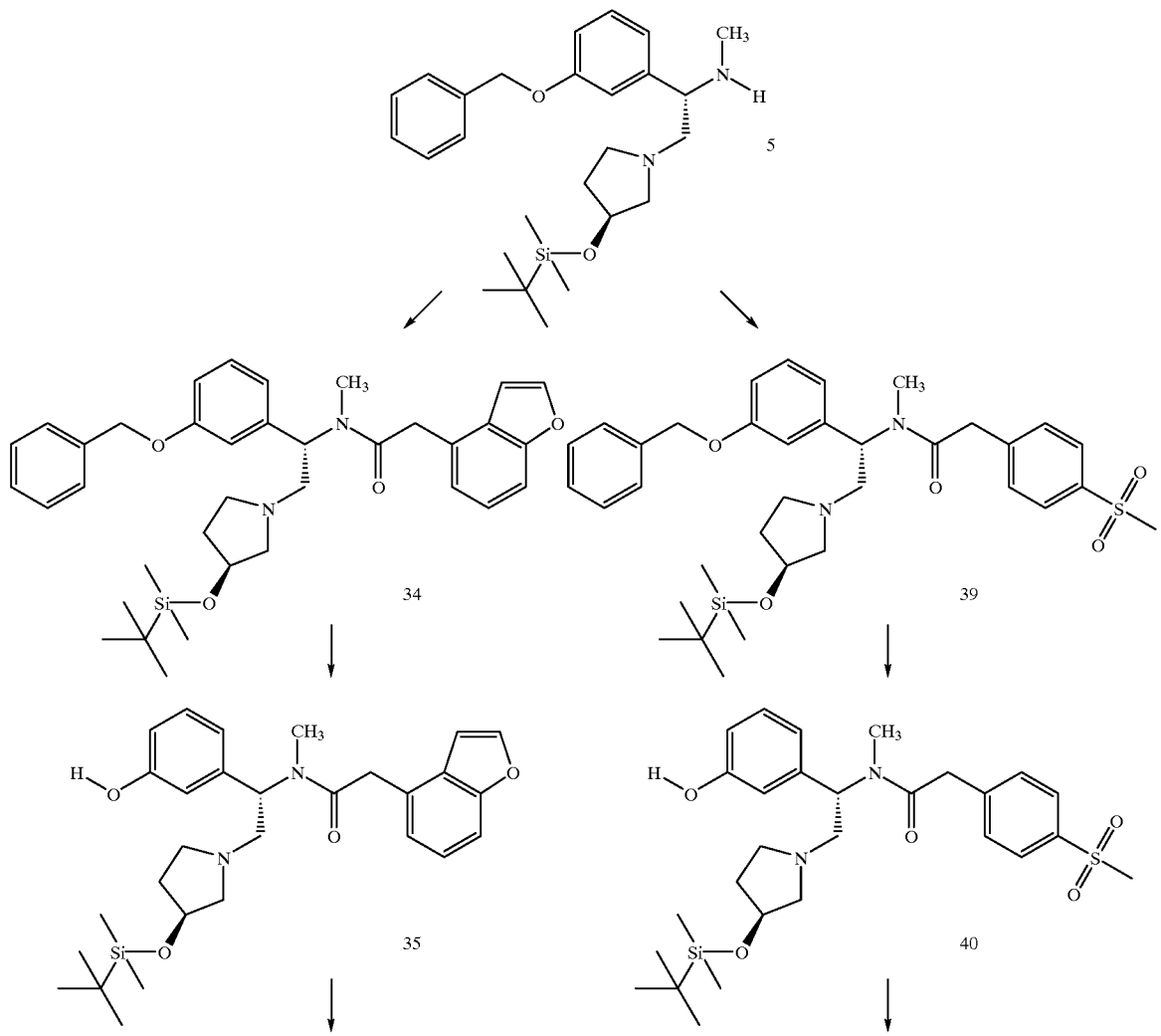

17 18
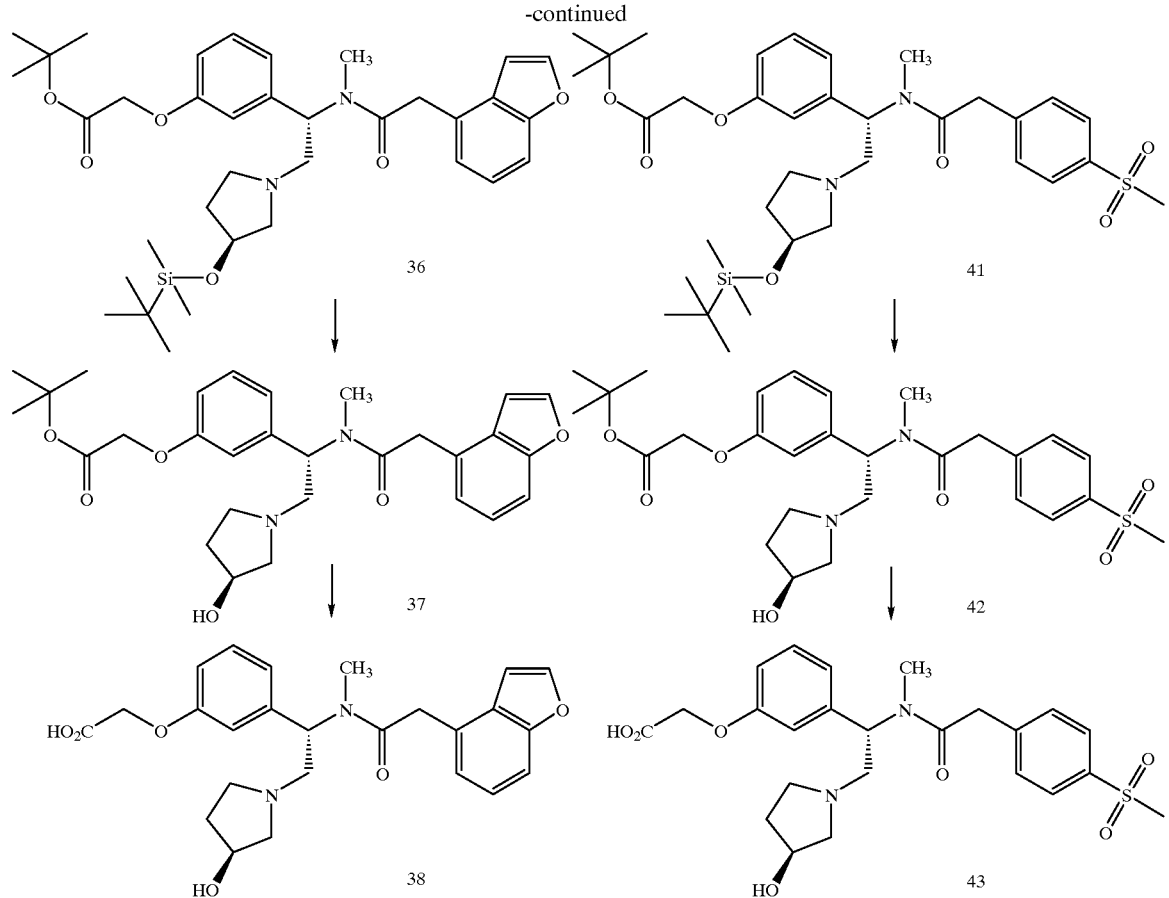
Scheme 6
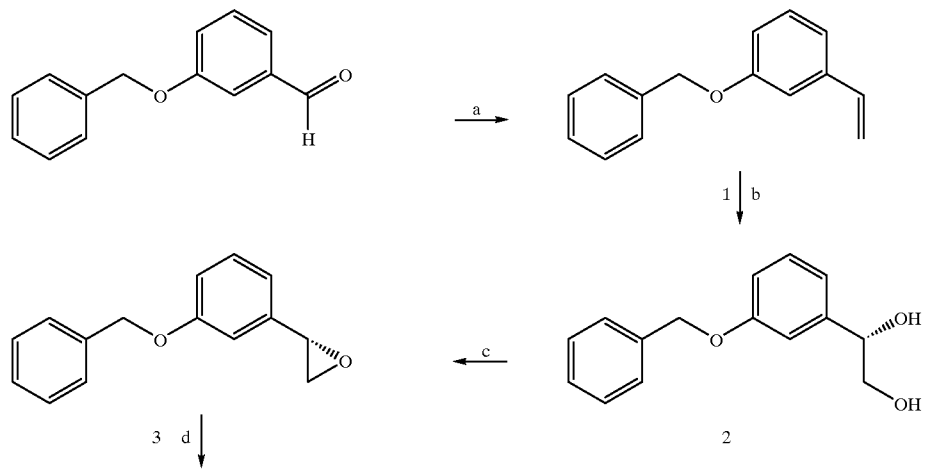

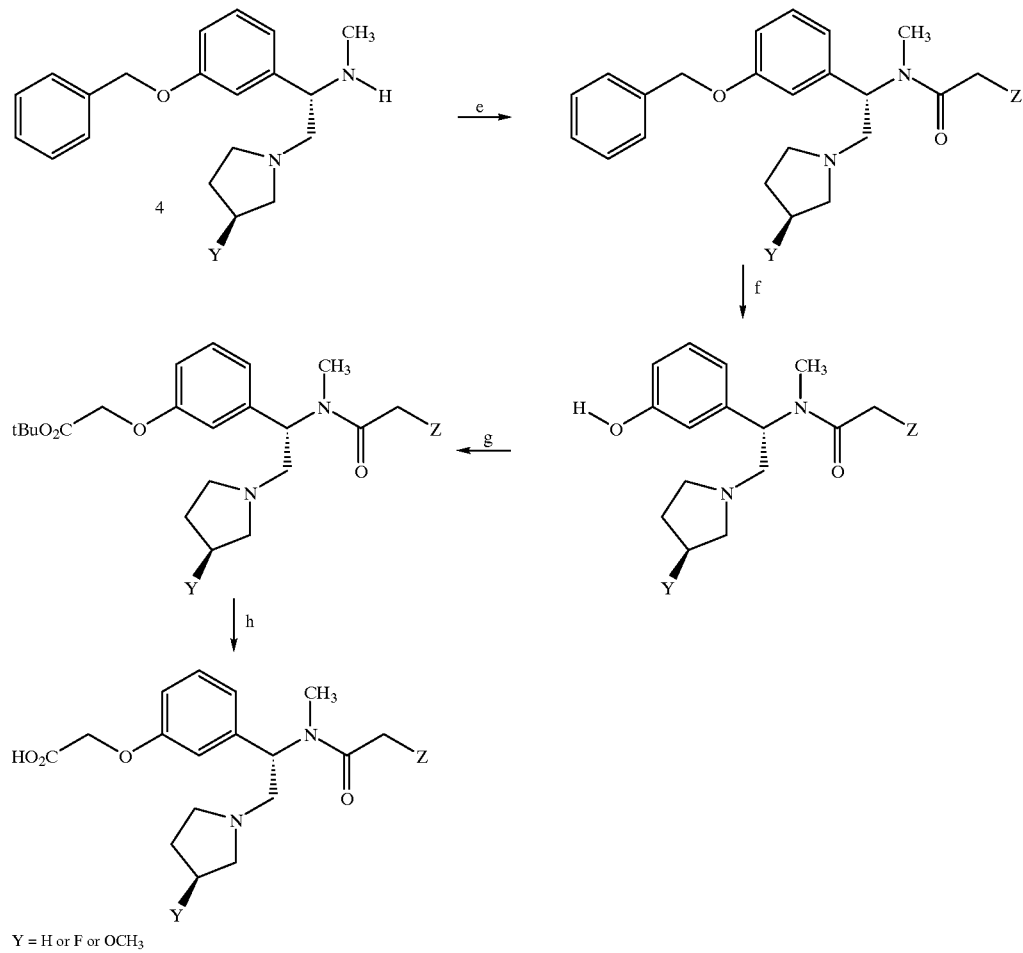

Y = H or F or OCH₃

Reactions and conditions:
a) Ph₃P+CH₃Br⁻, BuLi, THF, −20° C.; b) AD-mix-α. H₂O-ᵗBuOH; c) Me₃ SiCl, MeC(OMe)₃, CH₂Cl₂ then K₂CO₃ MeOH;
d) pyrrolidine, ethanol, 90° C., then concentrate: ether, MeSO₂Cl, Et₃N, then MeNH₂ (aqueous);
e) CDI, ZCH₂CO₂H, THF; f)H₂. Pd/C. Ethanol; g) BrCH₂CO₂tBu, K₂CO₃, DMF; h) HCl.

Description of Scheme 6

The starting aldehyde is converted into the corresponding styrene by means of a Wittig reaction in a suitable solvent. Asymmetric dihydroxylation gives a diol, and this is converted into an epoxide. Opening the epoxide with pyrrolidine or a substituted pyrrolidine leads to an amino alcohol which can then be transformed into a diamine. Coupling the diamine with an acid using a suitable coupling reagent leads to an amide. The benzyl protecting group is removed by hydrogenation with a catalyst in a suitable solvent. The phenol is then etherified with a suitable base and t-butylbromoacetate. Conversion of the ester into the carboxylic acid by means of a strong acid leads to the salts of the final compound.

Scheme 7

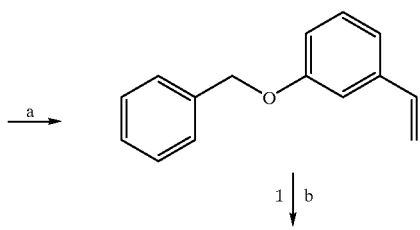

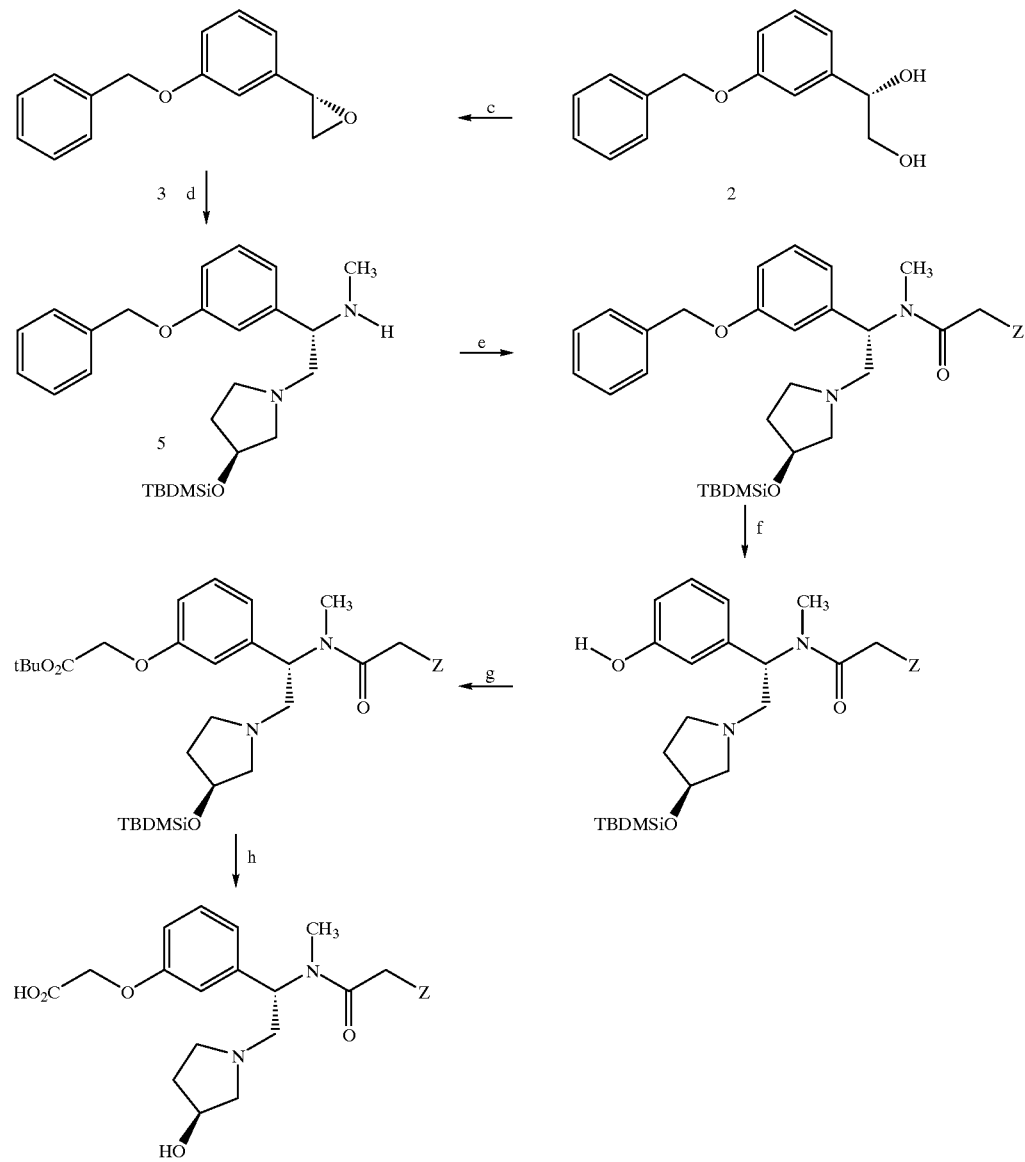

Reactions and conditions:
a) Ph₃P⁺CH₃Br⁻, BuLi THF, −20° C.; b) AD-mix-α, H₂O-ᵗBuOH; c) Me₃SiCl, MeC(OMe)₃,
d) pyrrolidine, ethanol, 90° C., then concentrate: ether, MeSO₂Cl, Et₃N, then MeNH₂ (aqueous);
e) CDI, ZCH₂CO₂H, THF; f)H₂. Pd/C. Ethanol; g) BrCH₂CO₂tBu, K₂CO₃, DMF; h) HCl.
TBDMS=tert-butyldimethylsilyl Description of Scheme 7

The starting aldehyde is converted into the corresponding styrene by means of a Wittig reaction in a suitable solvent. Asymmetric dihydroxylation gives a diol, and this is converted into an epoxide. Opening the epoxide, the hydroxy protected pyrrolidine leads to an amino alcohol which can then be transformed into a diamine. Coupling the diamine with an acid using a suitable coupling reagent leads to an amide. The benzyl protecting group is removed by hydrogenation with a catalyst in a suitable solvent. The phenol is then etherified with a suitable base and t-butylbromoacetate. The protecting group is removed from the hydroxy pyrrolidine. Conversion of the ester into the carboxylic acid by means of a strong acid leads to the salts of the final compound.

Scheme 8

(S)-(3-{1-[(Thianaphthen-2-yl-acetyl)-methyl-amino]-2-pyrrolidin-1-yl-ethyl}-phenoxy)-acetic acid

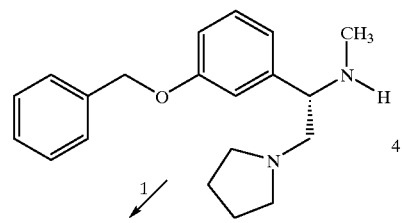

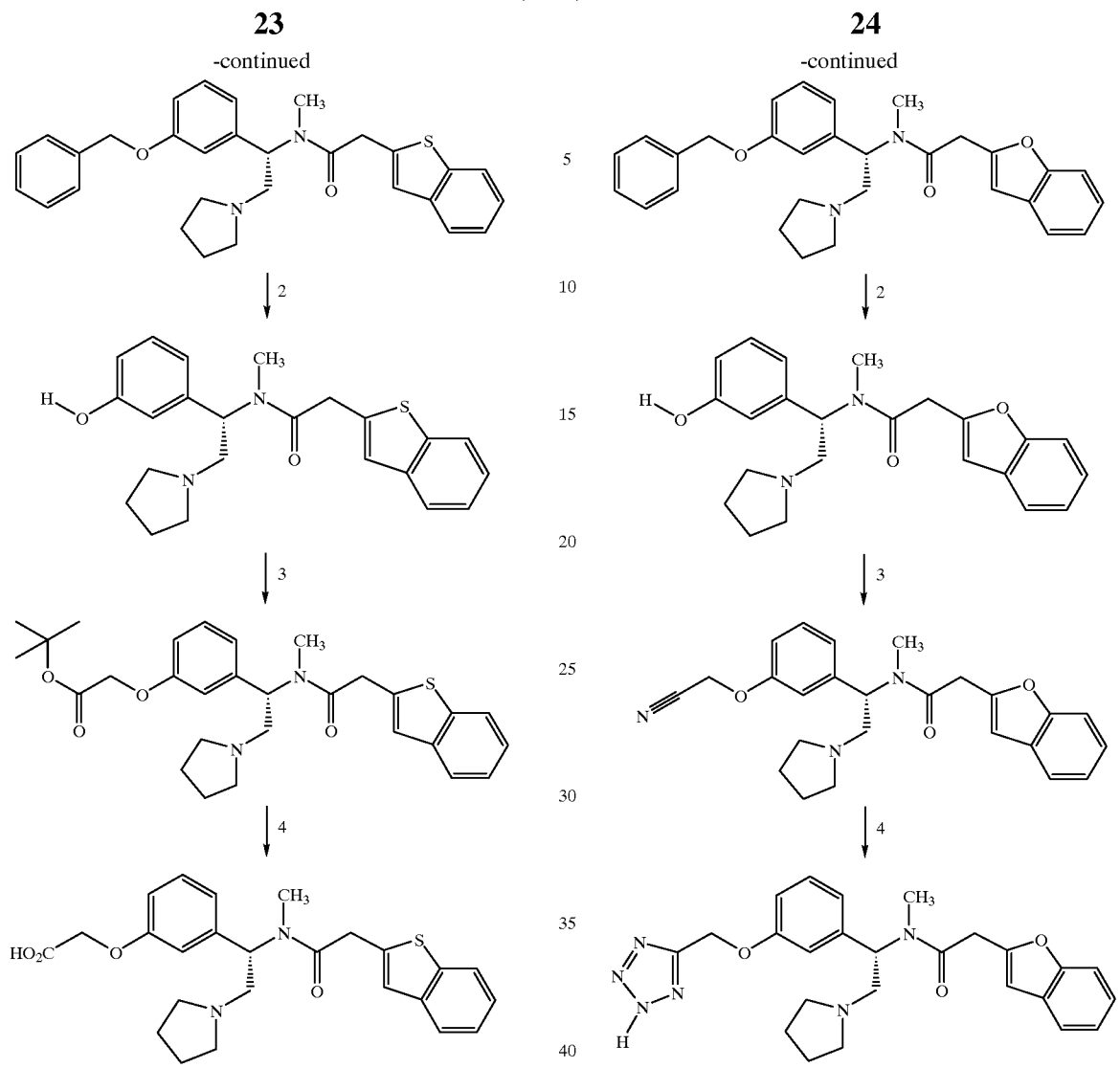

Reactions and Conditions:
1) Carbonyl diimidazole, 2-benzothiophene acetic acid
2) H₂, catalyst, 3) t-Butylbromoacetate, K₂CO₃, 4) HCl Scheme 9

(S)-2-Benzofuran-2-yl-N-methyl-N-{2-pyrrolidin-1-yl-1-[3-(2H-tetrazol-5-ylmethoxy)-phenyl]-ethyl}-acetamide Reactions and Conditions:

1) Carbonyl diimidazole, 2-benzofuran acetic acid

2) H₂, catalyst

3) Bromoacetonitrile, K₂CO₃

4) NH₄Cl, NaN₃

Scheme 10

[S-(R*,R*)]-{3-[1-[(Benzofuran-4-yl-acetyl)-methyl-amino]-2-(3-fluoro-pyrrolidin-1-yl)-ethyl]-phenoxy}-acetic acid

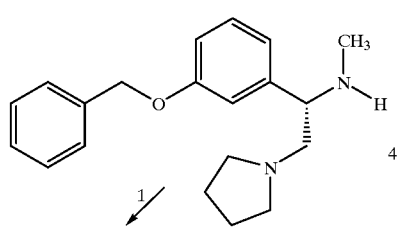

25 26
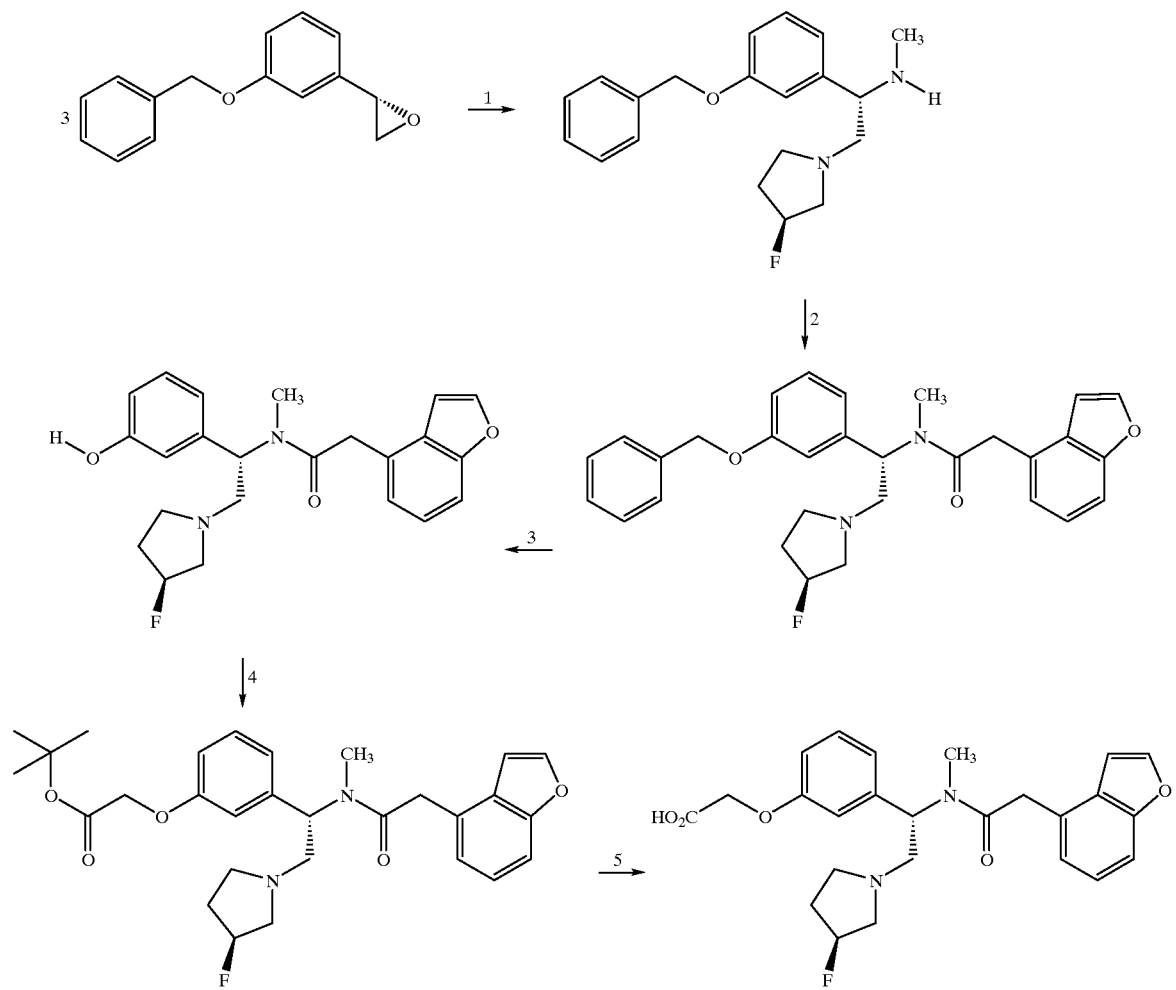
Reactions and Conditions:
1) 3-fluoropyrrolidine then MeSO₂Cl, Et₃N, MeNH₂
2) 4-benzofuranacetic acid, carbonyl diimidazole
3) H₂, catalyst, 4) t-Butylbromoacetate, K₂CO₃, 5) HCl
Scheme 11
(S)-(3-{1-[(Benzofuran-2-yl-acetyl)-methyl-amino]-2-pyrrolidin-1-yl-ethyl}-phenoxy)-methanesulfonic acid
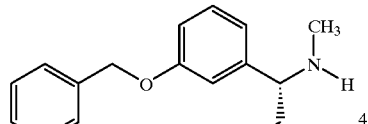
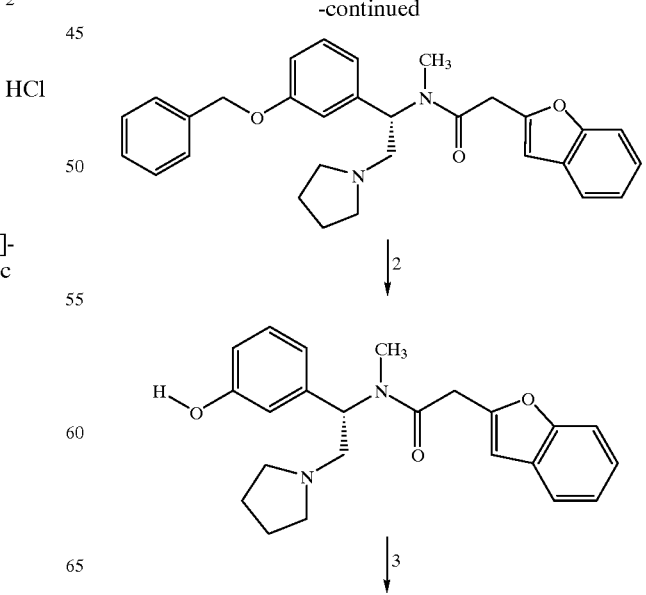

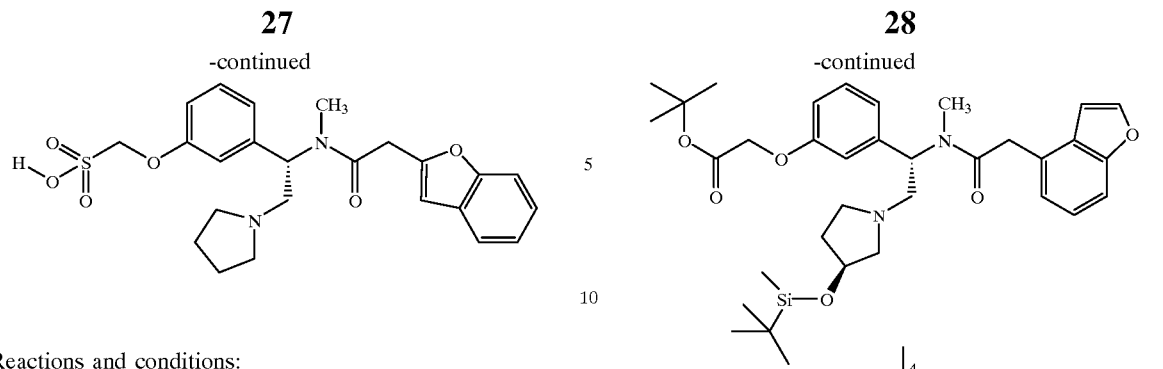

Reactions and conditions:

1) Carbonyl diimidazole, 2-benzofuran acetic acid
2) H₂, catalyst
3) ClCH₂SO₃Na, NaOH Scheme 12

[S-(R*,R*)]-3-[1-[(Benzofuran-4-yl-acetyl)-methyl-amino]-2-(3-methoxy-pyrlrolidin-1-yl)-ethyl]-phenoxy)-acetic acid

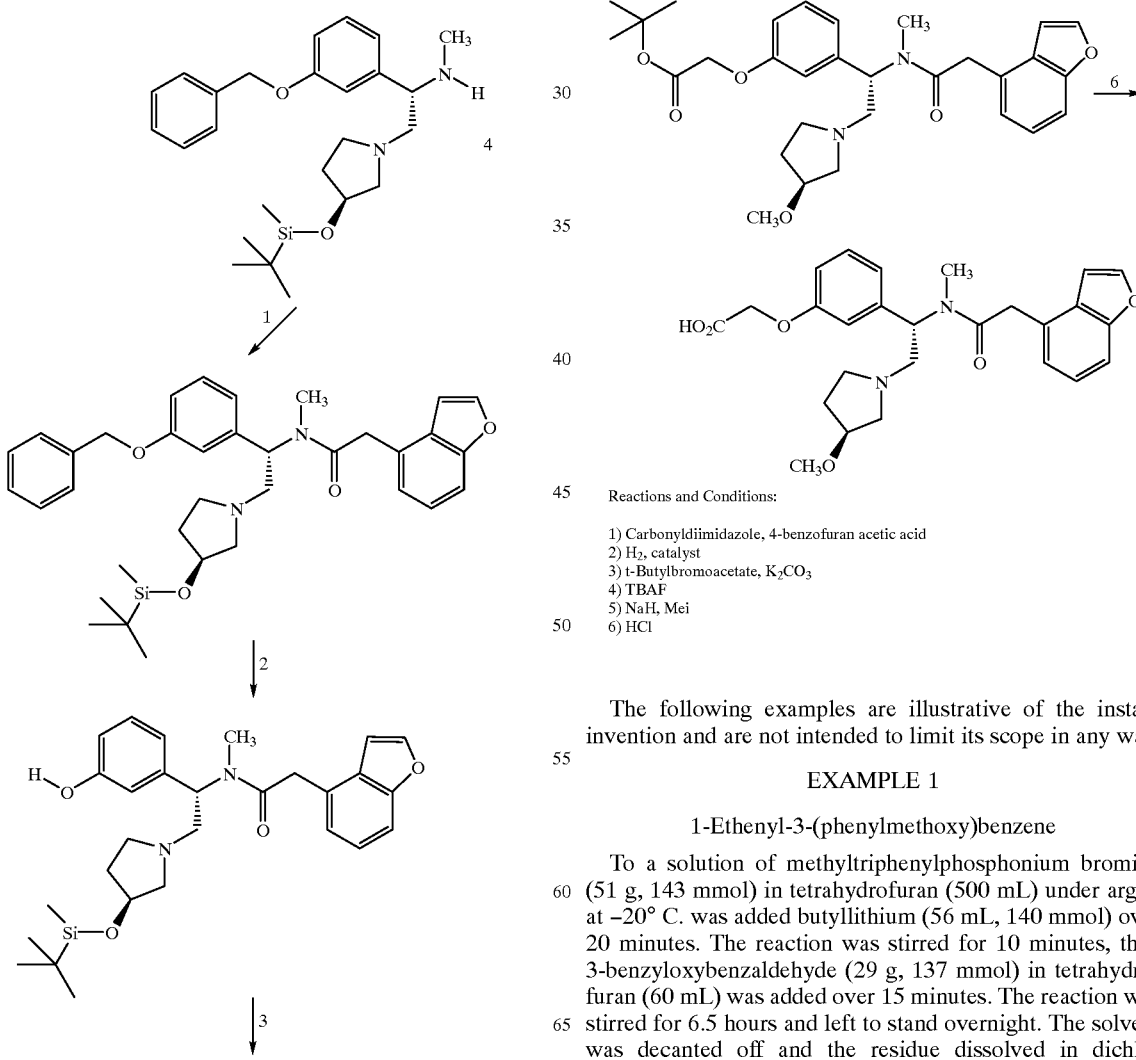

Reactions and Conditions:

1) Carbonyldiimidazole, 4-benzofuran acetic acid
2) H₂, catalyst
3) t-Butylbromoacetate, K₂CO₃
4) TBAF
5) NaH, MeI
6) HCl The following examples are illustrative of the instant invention and are not intended to limit its scope in any way.

EXAMPLE 1

1-Ethenyl-3-(phenylmethoxy)benzene

To a solution of methyltriphenylphosphonium bromide (51 g, 143 mmol) in tetrahydrofuran (500 mL) under argon at −20° C. was added butyllithium (56 mL, 140 mmol) over 20 minutes. The reaction was stirred for 10 minutes, then 3-benzyloxybenzaldehyde (29 g, 137 mmol) in tetrahydrofuran (60 mL) was added over 15 minutes. The reaction was stirred for 6.5 hours and left to stand overnight. The solvent was decanted off and the residue dissolved in dichloromethane (100 mL) and extracted with a heptane/diethyl ether mixture (9:1) until all the product was removed. The combined organics were filtered through silica and the solvent removed in vacuo to give the product as a clear oil, 122 mmol, 89%.

$^1$H NMR (400 MHz, CDCl$_3$): δ7.45–7.32 (5H, m); 7.26–7.22 (1H, m); 7.04–7.01 (2H, m); 6.89–6.87 (1H, m); 6.68 (1H, dd, J=17.6, 10.8 Hz); 5.73 (1H, dd, J=17.6, 0.8 Hz); 5.24 (1H, dd, J=10.8, 0.8 Hz); 5.08 (2H, s). IR (thin film) ν=3033.0, 1598.0, 1575.0, 1489.0, 1443.0, 1259.0.

EXAMPLE 2

(S)-1-(3-Benzyloxy-phenyl)-ethane-1,2-diol

At 0° C. were combined t-butyl alcohol (150 mL), water (150 mL), and AD-mix-α (42 g). Example 1 (6.4 g, 30 mmol) was added and stirred for 3.5 hours. The reaction was refrigerated overnight (15.5 hours), stirred for 8 hours, refrigerated for another 16 hours, and stirred for a further 1 hour. Sodium sulphite (45 g, 36 mmol) was added and the reaction stirred for 2 hours at room temperature. The mixture was poured into ethyl acetate (300 mL) and the aqueous extracted with ethyl acetate (3×150 mL). The organics were dried (MgSO$_4$) and the solvent removed in vacuo. Purification by column chromatography (ethyl acetate:heptane 9:1) gave the product as a yellow oil, 30 mmol, 100%.

$^1$H NMR (400 MHz, CDCl$_3$): δ7.45–7.28 (6H, m); 7.03 (1H, s); 6.96–6.90 (2H, m); 5.07 (2H, s); 4.80 (1H, ddd, J=7.6, 3.6, 3.6 Hz), 3.77 (1H, ddd, J=11.6, 7.6, 3.6 Hz); 3.66(1H, ddd, J=11.6, 7.6, 4.8 Hz); 2.50 (1H, d, J=3.6 Hz); 2.02 (1H, dd, J=7.6, 4.8 Hz). IR (thin film) ν=3363.0, 1586.0, 1489.0, 1449.0, 1264.0.

EXAMPLE 3

(S)-2-(3-Benzyloxy-phenyl)-oxirane

To a solution of Example 2 (16.22 g, 66 mmol) in dichloromethane (150 mL), trimethylorthoacetate (10.0 mL, 79 mmol) and chlorotrimethylsilane (10.0 mL, 79 mmol) were added. The reaction was stirred at room temperature under argon for 2 hours, then the solvent removed in vacuo. Potassium carbonate (11.59 g, 84 mmol) and methanol (260 mL) were added, and the reaction was stirred at room temperature under argon for 2 hours then poured into saturated ammonium chloride solution (550 mL) and extracted with dichloromethane (1650 mL). The organics were dried (MgSO$_4$) and the solvent removed in vacuo. Column chromatography (heptane:ethyl acetate 4:1) gave the product as a yellow oil, 56 mmol, 85%.

$^1$H NMR (400 MHz, CDCl$_3$): δ7.44–7.24 (6H, m); 6.93–6.89 (3H, m); 5.06 (2H, s); 3.84 (1H, dd, J=4.0, 2.8 Hz); 3.12 (1H, d, J=5.6, 4.0 Hz); 2.77 (1H, J=5.6, 2.8 Hz). IR (thin film) ν=3035.0, 1586.0, 1495.0, 1455.0, 1240.0.

EXAMPLE 4

(S)-[1-(3-Benzyloxy-phenyl)-2-pyrrolidin-1-yl-ethyl]-methyl-amine

To a stirred solution of Example 3 (2.80 g, 12.4 mmol) in ethanol (45 mL), pyrrolidine (3.3 mL, 39.5 mmol) was added. The reaction was heated to reflux for 2.5 hours then all volatiles removed in vacuo. This was then dissolved in diethyl ether (60 mL), cooled to 0° C., and flushed with argon. Triethylamine (5.5 mL, 39 mmol) was added followed by methanesulphonyl chloride (1.2 mL, 16 mmol), and the reaction was stirred for 30 minutes. More triethylamine (3.7 mL, 26 mmol) was added, the reaction was warmed to room temperature over 30 minutes, then an aqueous solution of methylamine (40% w/w) (19 mL, 220 mmol) and water (16 mL) were added. After stirring for 18.5 hours, the layers were separated, and the aqueous layer was extracted with diethyl ether (3×100 mL). The combined organics were washed with 5% sodium bicarbonate solution (60 mL), water (60 mL) and brine (60 mL), dried (MgSO$_4$), and the solvent removed in vacuo. Purification by column chromatography (dichloromethane:methanol 9:1→dichloromethane:methanol:ammonia 40:9:1) gave the product as a yellow semi-solid, 9.0 mmol, 72%.

$^1$H NMR (400 MHz, CDCl$_3$): δ7.52–7.23 (6H, m); 7.07–7.05 (1H, m); 7.00–6.86 (2H, m); 5.07 (2H, s); 3.60 (1H, dd, J=10.8, 3.6 Hz); 2.88 (1H, t, J=10.8 Hz); 2.68–2.66 (2H, m); 2.53–2.47 (2H, m); 2.30 (3H, s); 2.38–2.14 (1H, m); 1.84–1.75 (4H, m). MS (ES$^+$)=311.12 C$_{20}$H$_{27}$N$_2$Oi$^+$ requires 311.45.

EXAMPLE 5

[S-(R*,R*)]-{1-(3-Benzyloxy-phenyl)-2-[3-(tert-butyl-dimethyl-silanyloxy)-pyrrolidin-1-yl]-ethyl}-methyl-amine To a stirred solution of Example 3 (7.65 g, 38 mmol) in ethanol (120 mL) was added Example 11 (7.85 g, 35 mmol). This was heated to reflux for 3.5 hours, stood at room temperature overnight (17 hours), and heated to reflux for a further 2 hours. The solvent was removed in vacuo. This was then dissolved in diethyl ether (110 mL), cooled to 0° C., and flushed with argon. Triethylamine (10.5 mL, 75 mmol) was added followed by methanesulphonyl chloride (2.2 mL, 28 mmol), and the reaction was stirred for 30 minutes. More triethylamine (6.9 mL, 50 mmol) was added, the reaction was warmed to room temperature over 30 minutes, then an aqueous solution of methylamine (40% w/w) (38 mL, 441 mmol) and water (31 mL) were added. After stirring for 19 hours, the layers were separated, and the aqueous layer was extracted with diethyl ether (3×200 mL). The combined organics were washed with saturated sodium bicarbonate solution (120 mL), water (120 mL) and brine (120 mL), dried (MgSO$_4$), and the solvent removed in vacuo. Purification by column chromatography (dichloromethane:methanol 9:1) gave the product as a yellow oil, 16.5 mmol, 66%.

$^1$H NMR (400 MHz, CDCl$_3$): δ7.46–7.22 (6H, m); 7.04 (1H, s); 6.94 (1H, d, J=7.6 Hz); 6.88 (1H, dd, J=7.6, 2.0 Hz); 5.07(2H, s); 4.41–4.35 (1H, m); 3.57 (1H, dd, J=10.4, 3.2 Hz); 3.01 (1H, dd, J=9.6, 6.0 Hz); 2.82–2.72 (2H, m); 2.61 (1H, d, J=4.0 Hz); 2.40–2.32 (2H, m); 2.30 (3H, s); 2.13–2.03 (1H, m); 1.71–1.64 (1H, m); 0.89 (9H, s); 0.06 (6H, s). MS (ES$^+$)=441.10 C$_{26}$H$_{41}$N$_2$O$_2$Si$^+$ requires 441.72.

EXAMPLE 6

Benzofuran-3-yl-acetic acid methyl ester

A solution of 3-coumaranone (5.0 g, 37 mmol) and methyl(triphenylphosphoranylideneacetate) (13.5 g, 40 mmol) in toluene (70 mL) was heated to reflux for 25 hours. More toluene was added (50 mL), and after a further 5 hours, more methyl(triphenylphosphoranylideneacetate) (0.5 g, 1.5 mmol). After another 19 hours, a further 1.0 g (3.0 mmol) was added, and after a further 21 hours, the solvent was removed in vacuo. Column chromatography (heptane:ethyl acetate 4:1) gave the product as a brown oil, 33 mmol, 89%.

$^1$H NMR (400 MHz, CDCl$_3$): δ7.63 (1H, s); 7.58–7.47 (2H, m); 7.33–7.24 (2H, m); 3.73 (3H, s); 3.72 (2H, s).

EXAMPLE 7

Benzofuran-3-yl-acetic acid

A solution of Example 6 (6.23 g, 33 mmol) and lithium hydroxide monohydrate (1.45 g, 35 mmol) in tetrahydrofuran (50 mL), water (35 mL), and methanol (14 mL) was stirred for 6.5 hours at room temperature. Water (70 mL) was added, and the reaction mixture was acidified to pH 4 using 2 M HCl and extracted with dichloromethane (5×200 mL). The organics were dried (MgSO$_4$) and the solvent removed in vacuo to give a brown solid. This was dissolved in diethyl ether, heptane was added, and the mixture was stirred overnight. Solvent was removed by syringe to give product as a pale brown solid, 27 mmol, 80%.

$^1$H NMR (400 MHz, CDCl$_3$): δ7.64 (1H, s); 7.58–7.56 (1H, m); 7.50–7.48 (1H, m); 7.34–7.24 (2H, m); 3.76 (2H, s).

EXAMPLE 8

Benzofuran-2-yl-acetic acid methyl ester

A solution of 2-coumaranone (5.0 g, 37 mmol) and methyl(triphenylphosphoranylideneacetate) (13.5 g, 40 mmol) in toluene (70 mL) was heated to reflux for 25 hours. More toluene was added (10 mL), and after a further 5 hours, more methyl(triphenylphosphoranylideneacetate) (0.5 g, 1.5 mmol). After another 19 hours, a further 1.0 g (3.0 mmol) was added, and after a further 21 hours, the solvent was removed in vacuo. Column chromatography (heptane:ethyl acetate 4:1) gave the product as a brown oil, 28 mmol, 75%.

$^1$H NMR (400 MHz, CDCl$_3$): δ7.53–7.43 (2H, m); 7.27–7.18 (2H, m); 6.63 (1H, s); 3.84 (2H, s); 3.76 (3H, s).

EXAMPLE 9

Benzofuran-2-yl-acetic acid

A solution of Example 8 (5.32 g, 28 mmol) and lithium hydroxide monohydrate (1.24 g, 30 mmol) in tetrahydrofuran (45 mL), water (30 mL), and methanol (12 mL) was stirred for 5 hours at room temperature. Water (60 mL) was added, and the reaction mixture was acidified to pH 4 using 2 M HCl and extracted with dichloromethane (5×150 mL). The organics were dried (MgSO$_4$) and the solvent removed in vacuo. Column chromatography (ethyl acetate:heptane 4:1→ethyl acetate:methanol) gave a brown solid. This was dissolved in ethyl acetate, heptane was added, and the mixture was stirred overnight. Solvent was removed by syringe to give product as a pale brown solid, 17 mmol, 61%.

$^1$H NMR (400 MHz, CDCl$_3$): δ7.54–7.52 (1H, m); 7.46–7.44 (1H, m); 7.28–7.19 (2H, m); 6.66 (1H, s); 3.88 (2H, s).

EXAMPLE 10

(S)-1-Benzyl-3-(tert-butyl-dimethyl-silanyl)-pyrrolidine

To a solution of t-butyldimethylsilyl chloride (15 g, 100 mmol) in dichloromethane (30 mL) under argon, imidazole (8.7 g, 128 mmol) in dichloromethane (30 mL) was added, followed by S-(−)-1-benzyl-3-pyrrolidinol (15 g, 85 mmol) in dichloromethane (15 mL). The reaction was stirred at room temperature for 4 hours, then poured into water (300 mL) and extracted with dichloromethane (3×300 mL). The organics were dried (MgSO$_4$) and the solvent removed in vacuo. Column chromatography (ethyl acetate:heptane 4:1→ethyl acetate 100%) gave the product as a yellow oil, 85 mmol, 100%.

$^1$H NMR (400 MHz, CDCl$_3$): δ7.28–7.18 (5H, m); 4.38–4.33 (1H, m); 3.62 (1H, d, J=12.8 Hz); 3.54(1H, d, J=12.8 Hz); 2.87(1H, dd, J=9.6, 6.4 Hz); 2.63–2.52 (2H, m); 2.29 (1H, dd, J=9.6, 4.8 Hz); 2.12–2.03 (1H, m); 1.69–1.63 (1H, m); 0.87 (9H, s); 0.03 (3H, s); 0.02 (3H, s).

EXAMPLE 11

(S)-3-(tert-Butyl-dimethyl-silanyl)-pyrrolidine

To a solution of Example 10 (24.78 g, 85 mmol) in ethanol (200 mL) was added palladium catalyst (10% on carbon) (6.0 g) and HCl (4 M in dioxane) (4.5 mL, 18 mmol). This was hydrogenated at 30° C. for 6 hours and then filtered through Celite. The solvent was removed in vacuo, and column chromatography (ethyl acetate:methanol:ammonia 40:9:1) gave the product as a yellow oil, 82 mmol, 96%.

$^1$H NMR (400 MHz, CDCl$_3$): δ4.38–4.35 (1H, m); 3.18–3.12 (1H, m); 2.95–2.87 (3H, m); 1.90–1.86 (1H, m); 1.72–1.70 (1H, m); 0.88 (9H, s); 0.06 (6H, s). MS(ES$^+$)= 202.22 C$_{10}$H$_{24}$NOSi$^+$ requires 202.40. IR (thin film) ν=2930.0, 1417.0, 1254.0.

EXAMPLE 12

(S)-2-Benzofuran-2-yl-N-[1-(3-benzyloxy-phenyl)-2-pyrrolidin-1-yl-ethyl]-N-methyl-acetamide To a solution of 2-benzofuran acetic acid (0.861 g, 4.89 mmol) in THF (10 mL) at room temperature was added carbonyldiimidazole (0.856 g, 5.28 mmol). After stirring for 2 hours, a solution of Example 4 (1.419 g, 4.57 mmol) in THF (10 mL) was added. After stirring for 14 hours, all volatiles were removed in vacuo and the residue resuspended in ethyl acetate (200 mL). This solution was washed with saturated sodium hydrogencarbonate solution, then water, then saturated NaCl solution (50 mL of each). After drying (MgSO$_4$) and concentration in vacuo, column chromatography (ethyl acetate) gave the desired product, 1.977 g, 92%.

$^1$H NMR (400 MHz, CDCl$_3$): δ7.53–7.16 (10H); 6.96–6.65 (4H, m); 6.10 (1H, d, J=10.7, 5.6 Hz); 5.21 (1H, minor rotamer); 5.03 (2H, s); 4.85 (2H, minor rotamer); 4.11 (1 H, minor rotamer); 3.92 (2H, m); 3.17 (1H, t, J=11.2 Hz); 3.04–2.96 (2H, minor rotamer); 2.73 (3H, s); 2.75–2.70 (2H, m); 2.58–2.49 (2H, m); 1.76 (2H, m); 1.58 (2H, m).

EXAMPLE 13

(S)-2-Benzofuran-2-yl-N-[1-(3-hydroxy-phenyl)-2-pyrrolidin-1-yl-ethyl]-N-methyl-acetamide A solution of Example 12 (1.970 g, 4.20 mmol) in absolute ethanol (50 mL) with Pearlman's catalyst (0.88 g) was hydrogenated at 30° C. and 50 psi for 5.5 hours. The catalyst was removed by filtration through Celite and concentrated in vacuo to give the product, 1.391 g, 87%. This was used without further purification.

EXAMPLE 14

(S)-2-Benzofuran-2-yl-N-[1-(3-hydroxy-phenyl)-2-pyrrolidin-1-yl-ethyl]-N-methyl-acetamide To a solution of Example 13 (1.390 g, 3.67 mmol) in DMF (20 mL) was added powdered potassium carbonate (1.528 g, 11.07 mmol) followed by t-butylbromoacetate (0.65 mL, 4.03 mmol). After stirring for 22 hours, the solution was diluted with water (50 mL) and extracted with dichloromethane (3×100 mL). The combined organic phases were dried (MgSO$_4$) and concentrated in vacuo. Purification by column chromatography in ethyl acetate:methanol:aqueous ammonia (90:9:1) gave an inseparable mixture of product and an unidentified side product. This was used in the next step without any further attempt at purification.

EXAMPLE 15

(S)-(3-{1-[(Benzofuran-2-yl-acetyl)-methyl-amino]-2-pyrrolidin-1-yl-ethyl}-phenoxy)-acetic acid To a solution of crude Example 14 (0.482 g, 0.98 mmol) in dichloromethane (2 mL) was added HCl (2 mL of 4 M solution in dioxan). After stirring for 16 hours, all volatiles were removed in vacuo and the resulting solid dissolved dichloromethane. A small amount of diethyl ether was added and the suspension left for 5 minutes, in which time a beige solid precipitated out. The resulting supernatant was removed and diluted 100 times with diethyl ether to give a white suspension, which was allowed to settle. This solid was filtered and dried to give pure product, 0.305 g.

$^1$H NMR (400 MHz, CDCl$_3$): δ7.49 (1H, m); 7.48 (1H, d); 7.42–7.17 (3H, m); 6.91 (1H, s); 6.83 (1H, d); 6.80 (1H, d); 6.64 (1H, s); 6.35 (1H, br d); 4.65 (2H, m); 4.61 (1H, t); 4.58 (1H, d); 4.05 (1H, d); 3.15 (1H, br d); 2.85 (3H, s); 2.40–1.80 (8H, m).

LRMS (ES$^+$) Found 437.27 C$_{25}$H$_{29}$N$_2$O$_5{}^+$ requires 437.51.

EXAMPLE 16

(S)-2-Benzofuran-3-yl-N-[1-(3-henzyloxy-phenyl)-2-pyrrolidin-1-yl-ethyl]-N-methyl-acetamide To a solution of 3-benzofuran acetic acid (3.30 g, 18.73 mmol) in THF (16 mL) at room temperature was added carbonyldiimidazole (3.13 g, 19.32 mmol). After stirring for 2 hours, a solution of Example 4 (6.00 g, 19.32 mmol) in THF (10 mL) was added. After stirring for 16 hours, all volatiles were removed in vacuo and the residue resuspended in ethyl acetate (150 mL). This solution was washed with saturated sodium hydrogencarbonate solution, then water, then saturated NaCl solution (50 mL of each). After drying (MgSO$_4$) and concentration in vacuo, column chromatography (90:9:1 ethyl acetate:methanol:aq. NH$_3$) gave the desired product, 4.34 g, 49%.

$^1$H NMR (400 MHz, CDCl$_3$): δ7.78 (1H, s); 7.68 (1H, m); 7.46–7.19 (4H, m); 6.93–6.68 (3H, m); 6.13 (1H, dd, J=11.2, 5.1 Hz); 5.12 (1H, dd, minor rotamer); 4.98 (2H, AB q); 4.84 (2H, minor rotamer); 3.96–3.71 (4H, minor rotamer); 3.19 (1H, t, J=12.0 Hz), 3.00–2.94 (2H, minor rotamer); 2.79–2.65 (6H, m); 2.48 (2H, m); 1.75 (4H, m).

EXAMPLE 17

(S)-2-Benzofuran-3-yl-N-1-(3-hydroxy-phenyl)-2-pyrrolidin-1-yl-ethyl]-N-methyl-acetamide A solution of Example 16 (2.048 g, 4.37 mmol) in absolute ethanol (50 mL) with palladium on charcoal (0.85 g) was hydrogenated at 30° C. and 50 psi for 5.5 hours. The catalyst was removed by filtration through Celite and concentrate in vacuo to give the product, 1.466 g, 89%. This was used without further purification.

EXAMPLE 18

(S)-(3-{1-[(Benzofuran-3-yl-acetyl)-methyl-amino]-2-pyrrolidin-1-yl-ethyl}-phenoxy)-acetic acid tert-butyl ester To a solution of Example 17 (1.460 g, 3.86 mmol) in DMF (25 mL) was added powdered potassium carbonate (1.51 g, 22.5 mmol) followed by t-butylbromoacetate (0.80 mL, 4.95 mmol). After stirring for 24 hours, the solution was diluted with water (50 mL) and extracted with dichloromethane (4×100 mL). The combined organic phases were dried (MgSO$_4$) and concentrated in vacuo. Purification by column chromatography in 9:1 ethyl acetate:methanol gave the product as an oil, 1.272 g. 67%.

$^1$H NMR (400 MHz, CDCl$_3$): δ7.79 (1H, s); 7.57 (1H, m); 7.46 (1H, m); 7.31–7.19(3H, m); 6.94(1H, m); 6.88(1H br s); 6.79 (1H, m); 6.13 (1H, dd, J=11.2, 4.9 Hz); 5.13 (1H, minor rotamer); 4.46 (2H, s); 4.36 (2H, minor rotamer); 3.90–3.71 (2H, m); 3.20 (1H, m); 2.82–2.64 (6H, m); 2.50 (2H, m); 1.75 (4H, m); 1.49 (9H, s).

EXAMPLE 19

(S)-(3-{1-[(Benzofuran-3-yl-acetyl)-methyl-amino]-2-pyrrolidin-1-yl-ethyl}-phenoxy)-acetic acid To a solution of Example 18 (1.272 g, 2.58 mmol) in dichloromethane (10 mL) was added HCl (2.5 mL of 4 M solution in dioxan). After stirring for 24 hours, all volatiles were removed in vacuo and the resulting solid washed with acetonitrile. After removing the solvent, the resulting solid was dried to give a beige solid, 0.50 g.

$^1$H NMR (400 MHz, DMSO): δ13.02 (1H, br s); 10.50 (1H, br s); 7.85 (1H, s); 7.77 (1H, d, J=7.3 Hz); 7.54 (1H, d, J=8.1 Hz); 7.31–7.21 (31H, m); 6.89–6.81 (3H, m); 6.13 (1H, dd, J=12.0, 2.9 Hz); 4.14–3.91 (3H, m); 3.65–3.55 (3H, m); 3.33 (2H, s); 3.14 (2H, m); 2.90 (3H, s); 2.07–1.93 (4H, m). LRMS (ES$^+$) Found 437.01 C$_{25}$H$_{29}$N$_2$O$_5{}^+$ requires 437.51. Melting point: 196–201° C.

EXAMPLE 20

(S)-N-[1-(3-Benzyloxy-phenyl)-2-pyrrolidin-1-yl-ethyl]-2-(4-methanesulfonyl-phenyl)-N-methyl-acetamide To a solution of 4-methylsulphonylphenylacetic acid (1.03 g, 4.8 mmol) in tetrahydrofuran (12 mL) was added carbonyldiimidazole (0.84 g, 5.2 mmol). The reaction was stirred at room temperature under argon for 3 hours then the solvent was removed in vacuo. Example 4 (1.45 g, 4.7 mmol) in tetrahydrofuran (10 mL) was added and the reaction stirred for 63.5 hours at room temperature under argon. The solvent was removed in vacuo, and the residue was dissolved in ethyl acetate (180 mL) and washed with saturated sodium hydrogen carbonate solution (50 mL), water (50 mL), and brine (50 mL). The organics were dried (MgSO$_4$) and the solvent removed in vacuo. Column chromatography (ethyl acetate:methanol 9:1→4:1) gave the product as a white foam, 3.5 mmol, 75%.

$^1$H NMR (400 MHz, CDCl$_3$): δ7.89–7.87 (2H, m); 7.53–7.23 (8H, m); 6.92–6.74 (3H, m); 6.07 (1H, dd, J=10.8, 5.6 Hz); 5.05 (2H, s); 5.05–5.02 (1H rotamer, m); 3.90(1H, d, J=16.0 Hz); 3.80(11H, d, J=16.0 Hz); 3.14 (1H, t, J=11.6 Hz); 3.03 (3H, s); 3.03–2.97 (1H rotamer, m); 2.99 (3H rotamer, s); 2.81 (3H rotamer, s); 2.71 (3H, s); 2.71–2.65 (2H, m); 2.52–2.46 (3H, m); 1.75 (4H, br). IR (thin film) ν=2964.0, 2796.0, 1644.0, 1488.0, 1446.0, 1398.0, 1306.0.

EXAMPLE 21

(S)-N-[1-(3-Hydroxy-phenyl)-2-pyrrolidin-1-yl-ethyl]-2-(4-methanesulfonyl-phenyl)-N-methyl-acetamide To a solution of Example 20 (1.79 g, 3.5 mmol) in ethanol (85 mL) was added palladium hydroxide (20% on carbon)

(0.15 g). This was hydrogenated at 30° C. for 6 hours, filtered through Celite, and the solvent removed in vacuo to give a white foam, 3.4 mmol, 96%.

$^1$H NMR (400 MHz, CDCl$_3$): δ7.86–7.83 (2H, m); 7.50–7.43 (2H, m); 7.19–7.15 (1H, m); 6.82–6.69 (3H, m); 6.07 (1H, dd, J=10.8, 4.8 Hz); 5.02 (1H rotamer, br); 3.92–3.78 (2H, m); 3.23–3.19 (1H, m); 3.02 (3H, s); 3.00 (3H rotamer, s); 2.85 (3H rotamer, s); 2.75 (3H, s); 2.75–2.68 (3H, m); 2.58–2.52 (2H, m); 1.77 (4H, br).

EXAMPLE 22

(S)-[3-{[(4-Methanesulfonyl-phenyl)-acetyl]-methyl-amino}-2-pyrrolidin-1-yl-ethyl)-phenoxy]-acetic acid tert-butyl ester To a solution of Example 21 (1.41 g, 3.4 mmol) in dimethylformamide (22 mL) was added potassium carbonate (1.48 g, 10.7 mmol) and, under argon, t-butylbromoacetate (0.5 mL, 3.4 mmol). After stirring at room temperature for 22.5 hours, the reaction was poured into water (170 mL), extracted with dichloromethane (170 mL), dried (MgSO$_4$), and the solvent removed in vacuo. Purification by column chromatography (dichloromethane:methanol 19:1 followed by ethyl acetate::methanol:ammonia 90:9:1) gave the product as a yellow oil, 1.9 mmol, 56%.

$^1$H NMR (400 MHz, CDCl$_3$): δ7.89–7.87 (2H, m); 7.53–7.45 (2H, m); 7.26–7.22 (1H, m); 6.94–6.75 (3H, m); 6.07 (1H, dd, J=11.2, 4.8 Hz); 5.03–5.02 (1H rotamer, m); 4.49 (2H, s); 3.90 (1H, d, J=16.0 Hz); 3.80 (1H, d, J=16.0 Hz); 3.15 n(1H, t, J=11.6 Hz); 3.04 (3H, s); 3.03 (3H rotamer, s); 2.99–2.97 (1H rotamer, m); 2.82 (3H rotamer, s); 2.73 (3H, s); 22.73–2.64 (3H, m); 2.52–2.46 (2H, m); 1.74 (4H, br); 1.50 (9H, s). MS (ES$^+$)=531.00 C$_{28}$H$_{39}$N$_2$O$_6$S$^+$ requires 531.70.

EXAMPLE 23

(S)-[3-{[(4-Methanesulfonyl-phenyl)-acetyl]-methyl-amino}-2-pyrrolidin-1-yl-ethyl)-phenoxy]-acetic acid tert-butyl ester To a solution of Example 22 (1.0 g, 1.9 mmol) in dichloromethane (2 mL) was added HCl in dioxane (4.0 M) (1.0 mL) under argon. The reaction was stirred for 43 hours at room temperature and the solvent removed in vacuo. The residue was washed with dichloromethane and diethyl ether, then re-reacted using dichloromethane (1 mL) and HCl in dioxane (2 mL). After stirring for 66 hours, the solvent was removed and the solid washed with dichloromethane and diethyl ether. The product was obtained as the HCl salt; white solid, 1.8 mmol, 96%.

$^1$H NMR (400 MHz, CDCl$_3$): δ7.89–7.87 (2H, m); 7.57–7.52 (2H, m); 7.35–7.31 (1H, m); 7.00–6.96 (1H, m); 6.87–6.84 (2H, m); 6.35 (1H, d, J=10.0 Hz); 4.66 (1H, d, J=16.0 Hz); 4.56 (1H, d, J=15.6 Hz); 4.42(1H, t, J=12.8 Hz); 4.33 (1H, d, J=16.0 Hz); 3.78 (1H, d, J=16.4 Hz); 3.12 (1H, d, J=10.4 Hz); 3.05 (3H, s); 2.85 (3H, s); 2.10 (4H, br); 1.68 (4H, br). IR (thin film) ν=3380.5, 2924.0, 1644.0, 1294.0. Analysis Expected (1.7 HCl): C 53.72; H 5.96; N, 5.22. Obtained: C, 53.62; H, 6.26; N, 5.49. Melting point 115–118° C. MS (ES$^+$)=475.27 C$_{24}$H$_{31}$N$_2$O$_6$S$^+$ requires 475.59.

EXAMPLE 24

[S-(R*,R*)]-2-Benzofuran-3-yl-N-{1-(3-benzyloxy-phenyl)-2-[3-(tert-butyl-dimethyl-silanyloxy)-pyrrolidin-1-yl]-ethyl}-N-methyl-acetamide To a solution of 3-benzofuran acetic acid (1.446 g, 8.01 mmol) in THF (5 mL) at room temperature was added carbonyldiimidazole (1.31 g, 8.09 mmol). After stirring for 2 hours, a solution of Example 5 (2.68 g, 6.09 mmol) in THF (10 mL) was added. After stirring for 16 hours, all volatiles were removed in vacuo and the residue dissolved in ethyl acetate (300 mL). This solution was washed with saturated sodium hydrogencarbonate solution, then water, then saturated NaCl solution (50 mL of each). After drying (MgSO$_4$) and concentration in vacuo, column chromatography (60:40 ethyl acetate:heptane) gave the desired product, 3.04 g, 83%.

$^1$H NMR (400 MHz, CDCl$_3$): δ7.75 (1H, m); 7.59–7.57 (1H, m); 7.45–7.21 (9H, m); 6.89–6.67 (3H, m); 6.09 (1H, dd, J=11.2, 5.1 Hz); 5.09 (1H, minor rotamer); 4.98 (2H, m); 4.84 (2H, minor rotamer); 4.30 (1H, m); 3.95–3.72 (2H, m); 3.17–3.08 (2H, m); 3.02–2.89 (2H, minor rotamer); 2.86–2.69 (5H, m); 2.58 (1H, m); 2.37 (1H, m); 2.03 (1H, m); 1.68 (1H, m); 0.86 (9H, s); 0.04 (3H, s); 0.03 (3H, s).

EXAMPLE 25

[S-(R*,R*)]-2-Benzofuran-3-yl-N-[2-[3-(tert-butyl-dimethyl-silanyloxy)-pyrrolidin-1-yl]-1-(3-hydroxy-phenyl)-ethyl]-N-methyl-acetamide A solution of Example 24 (3.00 g, 5.01 mmol) in absolute ethanol (50 mL) with palladium on charcoal (0.34 g) was hydrogenated at 30° C. and 50 psi for 5.5 hours. The catalyst was removed by filtration through Celite and the filtrate concentrated in vacuo to give the product, 2.195 g. This was used without further purification.

EXAMPLE 26

[S-(R*,R*)]-(3-{1-[(Benzofuran-3-yl-acetyl)-methyl-amino]-2-[3-(tert-butyl-dimethyl-silanyloxy)-pyrrolidin-1-yl]-ethyl}-phenoxy)-acetic acid tert-butyl ester To a solution of Example 25 (2.195 g, 4.32 mmol) in DMF (40 mL) was added powdered potassium carbonate (1.21 g, 8.77 mmol) followed by t-butylbromoacetate (0.85 mmol, 5.26 mmol). After stirring for 18 hours, the solution was diluted with water (100 mL) and extracted with ethyl acetate (4×150 mL). The combined organic phases were dried (MgSO$_4$) and concentrated in vacuo. Purification by column chromatography in ethyl acetate:heptane (6:4) gave the product as an oil. Yield=1.209 g, 45%.

$^1$H NMR (400 MHz, CDCl$_3$): δ7.75 (1H, s); 7.58 (1H, m); 7.45 (1H, m); 7.31–7.20 (3H, m); 6.94–6.69 (3H, m); 6.09 (1H, dd, J=11.2, 4.9 Hz); 5.07 (1H, minor rotamer); 4.46 (2H, s); 4.42 (2H, minor rotamer); 4.30 (1H, m); 3.89–3.71 (2H, m); 3.18–3.08 (1H, m); 3.03–2.89 (2H, minor rotamer); 2.84 (1H, m); 2.77 (3H, s); 2.70 (1H, m); 2.54 (1H, m); 2.34 (1H, m); 2.00 (1H, m); 1.67 (1H, m); 1.57 (9H, s); 0.88 (9H, s); 0.04 (3H, s); 0.03 (3H, s).

EXAMPLE 27

[S-(R*,R*)]-{3-[1[-(Benzofuran-3-yl-acetyl)-methyl-amino]-2-(3-hydroxy-pyrrolidin-1-yl)-ethyl]-phenoxy}-acetic acid tert-butyl ester To a solution of Example 26 (1.20 g, 1.93 mmol) in THF (15 mL) at room temperature was added TBAF (2 mL of a 1 M solution in THF, 2 mmol). The reaction was stirred for 2 hours, then diluted with water (20 mL) and saturated brine (80 mL), and extracted with dichloromethane (4×120 mL). The combined organic phases were dried (MgSO$_4$) and concentrated in vacuo. Purification by column chromatography in ethyl acetate:methanol (9:1) gave the product as an oil. Yield=0.797 g, 81%.

¹H NMR (400 MHz, CDCl₃): δ7.72 (1H, s); 7.61 (1H, m); 7.48 (1H, m); 7.33–7.21 (3H, m); 6.93–6.74 (3H, m); 6.11 (1H, dd, J=11.5, 5.21 Hz); 5.11 (1H, minor rotamer); 4.47 (2H, s); 4.38 (2H, minor rotamer); 4.22 (1H, m); 3.87–3.72 (2H, m); 3.17 (1H, br t); 3.07 (1H, m); 2.85 (3H, s, minor rotamer), 2.79 (3H, s); 2.71–2.62 (3H, m); 2.26 (1H, m); 2.10 (1H, m); 1.58 (9H, s).

EXAMPLE 28

[S-(R*,R*)]-{3-[1-[(Benzofuran-3-yl-acetyl)-methyl-amino]-2-(3-hydroxy-pyrrolidin-1-yl)-ethyl]-phenoxy}-acetic acid To a solution of Example 27 (0.79 g, 1.55 mmol) in dichloromethane (12 mL) and water (0.5 mL) was added HCl (2.5 mL of 4 M solution in dioxan). After stirring for 24 hours, all volatiles were removed in vacuo to give a pale pink solid. The solid was stirred with ethyl acetate (75 mL) for 2 hours, then the solvent removed by pipette. This was repeated. The resulting solid was dissolved in acetonitrile (50 mL) and all solids removed by filtration. Ethyl acetate was added until the solution became cloudy, and the precipitate was allowed to settle. All supernatant was then removed and the resulting solid dried. Yield 0.25 g.

¹NMR (400 MHz, DMSO): δ13.0 (1H, br s); 10.86 (1H, br s); 7.85 (1H, br s); 7.76 (1H, br d); 7.54 (1H, d, J=8.1); 7.32–7.21 (3H, m); 6.89 (3H, m); 6.14 (1H, br d); 5.50 (1H, br s); 4.44 (1H, br s); 4.15–3.90 (4H, m); 3.65 (1H, br d); 3.51 (1H, br s); 3.33 (3H, s); 2.89 (3H, s); 2.27 (1H, m); 1.88 (1H, m). LRMS (ES−) Found 451.07 C₂₅H₂₇N₂O₆− requires 451.49. (ES+) Found 453.11 C₂₅H₂₉N₂O₆+ requires 453.07. Melting point 103–107° C. (amorphous solid).

EXAMPLE 29

[S-(R*,R*)]-2-Benzofuran-2-yl-N-{1-(3-benzyloxy-phenyl)-2-[3-(tert-butyl-dimethyl-silanyloxy)-pyrrolidin-1-yl]-ethyl}-N-methyl-acetamide To a solution of 2-benzofuran acetic acid (2.22 g, 12.60 mmol) in THF (40 mL) at room temperature was added carbonyldiimidazole (2.12 g, 13.07 mmol). After stirring for 4 hours, a solution of Example 5 (5.30 g, 12.03 mmol) in THF (30 mL) was added. After stirring for 16 hours, all volatiles were removed in vacuo and the residue dissolved in ethyl acetate (400 mL). This solution was washed with saturated sodium hydrogencarbonate solution, then water, then saturated NaCl solution (100 mL of each). After drying (MgSO₄) and concentration in vacuo, column chromatography (1:1 ethyl acetate:heptane) gave the desired product, 4.721 g, 66%.

¹H NMR (400 MHz, CDCl₃): δ7.52–7.13 (10H, m); 6.93–6.64 (4H, m); 6.05 (1H, dd, J=10.7, 5.4 Hz); 5.19 (1H, minor rotamer); 5.02 (2H, s); 4.84 (2H, AB q; minor rotamer); 4.33 (1H, m); 3.92 (2H, AB q); 3.17–3.10 (2H, m); 3.07–2.94 (2H, minor rotamer); 2.77 (5H, m); 2.67–2.60 (1H, m); 2.33 (1H, dd, J=9.5, 4.2 Hz); 2.05–1.96 (1H, m); 1.71–1.63 (1H, m); 0.87 (9H, s); 0.03 (3H, s); 0.02 (3H, s).

EXAMPLE 30

[S-(R*,R*)]-2-Benzofuran-2-yl-N-[2-[3-(tert-butyl-dimethyl-silanyloxy)-pyrrolidin-1-yl]-1-(3-hydroxy-phenyl)-ethyl]-N-methyl-acetamide A solution of Example 29 (4.72 g, 7.88 mmol) in absolute ethanol (50 mL) with 10% palladium on charcoal (0.37 g) added was hydrogenated at 30° C. and approximately 50 psi for 6 hours, after which the palladium on charcoal was removed by filtration through Celite and the filtrate concentrated in vacuo to give the product, 3.00 g, 75%. This was used without further purification.

EXAMPLE 31

[S-(R*,R*)]-(3-{1-[(Benzofuran-2-yl-acetyl)-methyl-amino]-2-[3-(tert-butyl-dimethyl-silanyloxy)-pyrrolidin-1-yl]-ethyl}-phenoxy)-acetic acid tert-butyl ester To a solution of Example 30 (3.00 g, 5.91 mmol) in DMF (48 mL) was added potassium carbonate (1.50 g, 10.87 mmol) followed by tert-butyl bromoacetate (1.20, 7.43 mmol). After stirring for 15 hours, the reaction mixture was poured into water (150 mL) and extracted with ethyl acetate (4×250 mL). The organic phases were dried (MgSO₄) and concentrated in vacuo. Purification by column chromatography (8:2 ethyl acetate:heptane) gave the product 1.659 g, 45%.

¹H NMR (400 MHz, CDCl₃): δ7.52–7.49 (1H, m); 7.43–7.39 (1H, m); 7.26–7.16 (3H, m); 6.95–6.64 (4H, m); 6.05 (1H, dd, J=11.0, 5.6 Hz; 5.18 (1H, minor rotamer); 4.48 (2H, s), 4.32 (1H, m); 3.95 (2H, AB q); 3.11 (2H, m); 2.79 (3H, s); 2.78 (1H, m); 2.63 (1H, m); 2.32 (1H, m); 2.01 (1H, m); 1.65 (1H, m); 1.57 (9H, s); 0.87 (9H, s); 0.03 (3H, s); 0.02 (3H, s).

EXAMPLE 32

[S-(R*,R*)]-{3-(1-[(Benzofuran-2-yl-acetyl)-methyl-amino]-2-(3-hydroxy-pyrrolidin-1-yl)-ethyl]-phenoxy}-acetic acid tert-butyl ester To a solution of Example 31 (1.659 g, 2.66 mmol) in THF (25 mL) at room temperature was added TBAF (2.8 mL of a 1 M solution in THF, 2.8 mmol). The reaction was stirred for 2.5 hours, then diluted with saturated brine (100 mL) and extracted with dichloromethane (4×120 mL). The combined organic phases were dried (MgSO₄) and concentrated in vacuo. Purification by column chromatography in ethyl acetate:methanol (9:1) gave the product as an oil. 0.824 g, 61%.

¹H NMR (400 MHz, CDCl₃): δ7.50 (1H, m); 7.42 (1H, m); 7.25–7.15 (3H, m); 6.94–6.63 (3H, m); 6.07 (1H, dd, J=11.0, 5.1 Hz); 5.20 (1H, minor rotamer); 4.48 (2H, s); 4.38 (2H, minor rotamer); 4.26 (1H, m); 4.02–3.86 (2H, AB q); 3.19–3.09 (2H, m); 2.80 (3H, s); 2.77–2.67 (3H, m); 2.25 (1H, m); 2.12 (1H, m); 1.69 (1H, m); 1.48 (9H, s).

EXAMPLE 33

[S-(R*,R*)]-{3-[1-[(Benzofuran-2-yl-acetyl)-methyl-amino]-2-(3-hydroxy-pyrrolidin-1-yl)-ethyl]-phenoxy}-acetic acid To a solution of Example 32 (0.824 g, 1.62 mmol) in dichloromethane (15 mL) was added HCl (3 mL of 4 M solution in dioxan). After stirring for 22 hours, all volatiles were removed in vacuo, and the resulting solid was washed with ethyl acetate (twice). The remaining solid was dissolved in acetonitrile and treated with diethyl ether. The precipitate was allowed to settle and the supernatant discarded. The solid was dried to give the product as an off-white solid.

¹H NMR (400 MHz, DMSO): δ12.97 (1H, br); 11.69 (1H, br); 7.59 (1H, m); 7.57 (1H, m); 7.34–7.19 (3H, m); 6.96–6.85 (3H, m); 6.75 (1H, s); 6.10 (1H, br d, J=9.5 Hz), 5.46 (1H, br); 4.68 (2H, s); 4.42 (1H, br s); 4.11 (2H, br s); 3.66 (1H, m); 2.83 (3H, s); 2.07 (1H, m); 1.99 (1H, m). IR (thin film) ν=3355 (br s), 2940 (m), 1733 (m), 1645 (s), 1454 (s). LRMS (ES+): Found 453.08 $C_{25}H_{29}N_2O_6$ requires 453.50.

EXAMPLE 34

[S-(R*,R*)]-2-Benzofuran-4-yl-N-{1-(3-benzyloxy-phenyl)-2-[3-(tert-butyl-dimethyl-silanyloxy)-2-pyrrolidin-1-yl]-ethyl}-N-methyl-acetamide To a solution of benzofuran-4-acetic acid (0.34 g, 1.9 mmol) in tetrahydrofuran (5 mL) was added carbonyldiimidazole (0.33 g, 2.0 mmol). The reaction was stirred at room temperature under argon for 3.5 hours, then the solvent was removed in vacuo. Example 5 (0.80 g, 1.8 mmol) in tetrahydrofuran (4 mL) was added and the reaction stirred for 18 hours at room temperature under argon. The solvent was removed in vacuo, and the residue was dissolved in ethyl acetate (70 mL) and washed with saturated sodium hydrogen carbonate solution (20 mL), water (20 mL) and brine (20 mL). The organics were dried (MgSO$_4$) and the solvent removed in vacuo. Column chromatography (ethyl acetate-:heptane 9:1) gave the product as a brown oil, 1.4 mmol, 75%.

$^1$H NMR (400 MHz, CDCl$_3$): δ5.60–7.59 (1H, m); 7.42–7.14 (10H, m); 6.92–6.82 (3H, m); 6.06 (1H, dd, J=10.4, 5.2 Hz); 5.05–5.02 (1H rotamer, m); 4.98 (1H, d, J=11.6 Hz); 4.93 (1H, d, J=11.6 Hz); 4.33–4.24 (1H, m); 4.03–3.92 (2H, m); 3.13–2.94 (2H, m); 2.87–2.67 (2H, m); 2.77 (3H rotamer, s); 2.69 (3H, s); 2.58–2.47 (1H, m); 2.31 (1H, dd, J=9.2, 4.4 Hz); 2.25 (1H rotamer, dd, J=9.2, 4.4 Hz); 2.02–1.92 (1H, m); 1.68–1.61 (1H, m); 0.88 (9H, s); 0.04 (3H, s); 0.03 (3H, s).

EXAMPLE 35

[S-(R*,R*)]-2-Benzofuran-4-yl-N-[2-[3-(tert-butyl-dimethyl-silanyloxy)-cyclopentyl]-1-(3-hydroxy-phenyl)-ethyl]-N-methyl-acetamide To a solution of Example 34 (1.97 g, 3.2 mmol) in methanol (70 mL) was added palladium hydroxide (20% on carbon) (0.10 g). This was hydrogenated at 30° C. for 6 hours, filtered through Celite, and the solvent removed in vacuo to give a white foam, 3.2 mmol, 97%. This was used without further purification.

$^1$H NMR (400 MHz, CDCl$_3$): δ7.59 (1H, s); 7.38 (1H, J=8.0 Hz); 7.23–7.00 (4H, m); 6.80–6.65 (3H, m); 6.20 (1H, br); 4.46 (1H, br); 4.22 (1H, br); 4.00 (1H, d, J=15.2 Hz); 3.71 (1H, d, J=15.6 Hz); 3.19–3.12 (3H, m); 2.83 (3H, s); 2.31 (1H, br); 1.86 (1H, br); 1.59 (2H, br); 0.84 (9H, s); 0.05 (6H, s).

EXAMPLE 36

[S-(R*,R*)]-(3-{1-[(Benzofuran-4-yl-acetyl)-methyl-amino]-2-[3-(tert-butyl-dimethyl-silanyloxy)-cyclopentyl]-ethyl}-phenoxy)-acetic acid tert-butyl ester To a solution of Example 35 1.63 g, 3.2 mmol) in dimethylformamide (22 mL) was added potassium carbonate (1.37 g, 9.9 mmol) and, under argon, t-butylbromoacetate (0.47 mL, 3.2 mmol). After stirring at room temperature for 23 hours, the reaction was poured into water (160 mL), extracted with dichloromethane (160 mL), dried (MgSO$_4$), and the solvent removed in vacuo. Purification by column chromatography (dichloromethane:methanol 39:1 followed by ethyl acetate-:heptane 4:1) gave the product as a clear oil, 1.4 mmol, 45%.

$^1$H NMR (400 MHz, CDCl$_3$): δ7.62–7.61 (1H, m); 7.41–7.14 (5H, m); 7.00–6.52 (3H, m); 6.05 (1H, dd, J=10.4, 5.2 Hz); 5.04–5.00 (1H rotamer, m); 4.44 (2H, d, J=1.6 Hz); 4.30–4.24 (1H, m); 4.01 (1H, d, J=15.6 Hz); 3.94 (1H, d, J=−15.6 Hz); 3.12–2.94 (2H, m); 2.86–2.68 (2H, m); 2.78 (3H rotamer, s); 2.71 (3H, s); 2.58–2.46 (1H, m); 2.30 (1H, dd, J=9.6, 4.0 Hz); 2.24 (1H rotamer, dd, J=9.6, 4.0 Hz); 2.02–1.92 (1H, m); 1.68–1.62 (1H, m); 1.50 (9H, s); 0.88 (9H, s); 0.04 (3H, s); 0.03 (3H, s).

EXAMPLE 37

[S-(R*,R*)]-{3-[1-[(Benzofuran-4-yl-acetyl)-methyl-amino]-2-(3-hydroxy-cyclopentyl)-ethyl]-phenoxy}-acetic acid tert-butyl ester To a solution of Example 36 (0.90 g, 1.45 mmol) in tetrahydrofuran (10 mL) was added tetrabutylammonium fluoride (1.0 M in tetrahydrofuran) (1.45 mL, 1.45 mmol). The reaction was stirred at room temperature under argon for 2.5 hours, then half the solvent was removed in vacuo. After stirring for a further 30 minutes, the reaction was poured into water (15 mL) and brine (70 mL), and extracted with dichloromethane (3×70 mL). The organics were dried (MgSO$_4$) and the solvent removed in vacuo. Column chromatography (ethyl acetate:methanol 4:1) gave the product as a clear oil, 1.32 mmol, 90%.

$^1$H NMR (400 MHz, CDCl$_3$): δ7.64–7.62 (1H, m); 7.43–7.14 (5H, m); 6.97–6.58 (3H, m); 6.08 (1H, dd, J=10.8, 5.2 Hz); 5.05–5.01 (1H rotamer, m); 4.45 (2H, s); 4.35 (2H rotamer, s); 4.17 (1H, br); 4.03 (1H, d, J=14.8 Hz); 3.96 (1H, d, J=14.8 Hz); 3.12–2.84 (2H, m); 2.82 (3H rotamer, s); 2.72 (3H, s); 2.69–2.48 (2H, m); 2.36 (1H rotamer, dd, J=9.6, 4.8 Hz); 2.20–2.04 (2H, m); 1.66–1.57 (2H, m); 1.50 (9H, s). MS (ES$^+$)=509.02 $C_{29}H_{37}N_2O_6$+ requires 509.63.

EXAMPLE 38

[S-(R*,R*)]-{3-[1-[(Benzofuran-4-yl-acetyl)-methyl-amino]-2-(3-hydroxy-cyclopentyl)-ethyl]-phenoxy}-acetic acid A solution of Example 37 (0.64 g, 1.25 mmol) in dichloromethane (2.0 mL) was stirred with HCl in dioxane (4.0 M) (0.8 mL, 3.20 mmol) for 24 hours at room temperature under argon. The solvent was removed, and the residue dissolved in dichloromethane (1.5 mL) and stirred with HCl in dioxane (1.5 mL, 6.0 mmol) for 47 hours. The solvent was removed in vacuo, and the residue washed with diethyl ether. The resultant solid was stirred in acetonitrile overnight, the acetonitrile was removed using a pipette, and diethyl ether was added to the acetonitrile. The solvent was removed in vacuo to give the HCl salt of the product as an off-white solid, 0.6 mmol, 51%.

$^1$H NMR (400 MHz, DMSO): δ7.93 (1H, s); 7.47–7.44 (1H, m); 7.31–7.09 (4H, m); 6.88–6.79 (3H, m); 6.13 (1H, dd, J=11.6, 2.4 Hz); 5.46 (1H, br); 4.66 (2H, s); 4.43 (1H, br); 4.17–4.03 (3H, m); 3.66–3.21 (4H, m); 2.85 (3H, s); 2.22 (21–1, br); 1.89 (1H, br). IR (thin film) ν=3391.0, 1634.0, 1435.0. MS (ES$^+$)=453.28 $C_{25}H_{29}N_2O_6$+ requires 453.52.

EXAMPLE 39

[S-(R*,R*)]-N-{1-(3-Benzyloxy-phenyl)-2-[3-(tert-butyl-dimethyl-silanyloxy)-cyclopentyl]-ethyl}-2-(4-methanesulfonyl-phenyl)-N-methyl-acetamide To a solution of 4-methylsulphonylphenylacetic acid (0.97 g, 4.5 mmol) in tetrahydrofuran (12 mL) was added carbonyldiimidazole (0.79 g, 4.9 mmol). The reaction was stirred at room temperature under argon for 3.75 hours, then the solvent was removed in vacuo. Example 5 (1.92 g, 4.4 mmol) in tetrahydrofuran (10 mL) was added and the reaction stirred for 18 hours at room temperature under argon. The solvent was removed in vacuo, and the residue was dissolved in ethyl acetate (170 mL) and washed with saturated sodium hydrogen carbonate solution (50 mL), water (50 mL) and brine (50 mL). The organics were dried ($MgSO_4$) and the solvent removed in vacuo. Column chromatography (dichloromethane:methanol 9:1 followed by ethyl acetate:methanol 19:1) gave the product as a brown oil, 3.8 mmol, 86%.

$^1$H NMR (400 MHz, $CDCl_3$): δ7.90–7.86 (2H, m); 7.52–7.23 (8H , m); 6.91–6.89 (3H, m); 6.04 (1H, dd, J=10.4, 4.8 Hz); 5.05 (2H, s); 4.35–4.34 (1H, m); 3.93–3.73 (2H, m); 3.12–3.06 (2H, m); 3.03 (3H, s); 2.99 (3H, rotamer, s); 2.80 (3H rotamer, s); 2.72 (3H, s); 2.84–2.72(2H, m); 2.65–2.54 (1H, m); 2.36 (1H, dd, J=9.2, 3.6 Hz); 2.05–2.01 (1H, m); 1.70–1.66 (1H, m); 0.89 (9H, s); 0.06 (3H, s); 0.05 (3H, s).

EXAMPLE 40

[S-(R*,R*)]-N-[2-[3-(tert-Butyl-dimethyl-silanyloxy)-cyclopentyl]-(3-hydroxy-phenyl)-ethyl]-2-(4-methanesulfonyl-phenyl)-N-methyl-acetamide To a solution of Example 39 (2.41 g, 3.8 mmol) in ethanol (220 mL) was added palladium hydroxide (20% on carbon) (0.15 g). This was hydrogenated at 30° C. for 16 hours, filtered through Celite, and the solvent removed in vacuo to give a white foam, 3.7 mmol, 97%. This was used without further purification.

$^1$H NMR (400 MHz, $CDCl_3$): δ7.92–7.86 (2H, m); 7.52–7.44 (2H, m); 7.22–7.17 (1H, m); 6.85–6.73 (3H, m); 6.02–6.11 (1H, m); 5.11 (1H rotamer, br); 4.35 (1H, br); 3.93–3.71 (1H, m); 3.13–3.03 (21–1, m); 3.03 (3H, s); 2.82 (3H rotamer, s); 2.75 (3H, s); 2.82–2.66 (2H, m); 2.57 (1H, m); 2.37–2.36 (1H, m); 2.06–2.00 (1H, m); 1.68 (1H, br); 0.88 (9H, s); 0.05 (3H, s); 0.04 (3H, s).

EXAMPLE 41

[S-(R*,R*)]-[3-(2-[3-(tert-Butyl-dimethyl-silanyloxy)-cyclopentyl]-1-{[(4-methanesulfonyl-phenyl)-acetyl]-methyl-amino}-ethyl)-phenoxy]-acetic acid tert-butyl ester To a solution of Example 59 (2.02 g, 3.7 mmol) in dimethylformamide (25 mL) was added potassium carbonate (1.58 g, 11 mmol) and, under argon, t-butylbromoacetate (0.55 mL, 3.7 mmol). After stirring at room temperature for 23 hours, the reaction was poured into water (180 mL), extracted with dichloromethane (180 mL), dried ($MgSO_4$), and the solvent removed in vacuo. Purification by column chromatography (ethyl acetate 100% →ethyl acetate:methanol 19:1) gave the product as a clear oil, 1.9 mmol, 50%.

$^1$H NMR (400 MHz, $CDCl_3$): δ7.90–7.87 (2H, m); 7.51–7.44 (2H, m); 7.26–7.22 (1H, m); 6.92–6.73 (3H, m); 6.03 (1H, dd, J=10.8, 5.2 Hz); 5.01–4.99 (1H rotamer, m); 4.49 (2H, s); 4.37–4.31 (1H, m); 3.89 (1H, d, J=16.0 Hz); 3.80 (1H, dd, J=16.0 Hz); 3.12–3.06 (2H, m); 3.09 (3H rotamer, s); 3.04 (3H, s); 2.84–2.71 (2H, m); 2.81 (3H rotamer, s); 2.73 (3H, s); 2.66–2.53 (1H, m); 2.44 (1H rotamer, dd, J=9.6, 4.0 Hz); 2.35 (1H, dd, J=9.6, 4.0 Hz); 2.07–1.88 (1H, m); 1.71–1.64 (1H, m); 1.50 (9H, s); 0.88 (9H, s); 0.05 (3H, S); 0.04 (3H, S).

EXAMPLE 42

[S-(R*,R*)]-[3-(2-(3-Hydroxy-cyclopentyl)-1-{[(4-methanesulfonyl-phenyl)-acetyl]-methyl-amino}-ethyl)-phenoxy]-acetic acid tert-butyl ester To a solution of Example 41 (1.23 g, 1.86 mmol) in tetrahydrofuran (3 mL) was added tetrabutylammonium fluoride (1.0 M in tetrahydrofuran) (1.9 mL, 1.9 mmol). The reaction was stirred at room temperature under argon for 4 hours, then the reaction was poured into water (20 mL). Brine (80 mL) was added, and the reaction extracted with dichloromethane (3×80 mL). The organics were dried ($MgSO_4$) and the solvent removed in vacuo. Column chromatography (dichloromethane:methanol 9:1) gave the product as a white foam, 1.54 mmol, 83%.

$^1$H NMR (400 MHz, $CDCl_3$): δ7.92–7.87 (2H, m); 7.53–7.46 (2H, m); 7.27–7.23 (1H, m); 6.92–6.75 (3H, m); 6.07 (1H, dd, J=10.8, 5.2 Hz); 4.99 (1H rotamer, t, J=7.2 Hz); 4.50 (2H, s); 4.27 (1H, m); 3.90 (1H, d, J=15.6 Hz); 3.82 (1H, d, J=15.6 Hz); 3.05 (3H, s); 3.22–2.98 (2H, m); 2.85 (3H rotamer, s); 2.75 (3H, s); 2.73–2.49 (2H, m); 2.43–2.04 (2H, m); 1.94–1.60 (2H, m); 1.50 (9H, s). MS ($ES^+$)=546.97 $C_{28}H_{39}N_2O_7S^+$ requires 547.70.

EXAMPLE 43

[S-(R*,R*)]-[3-(2-(3-Hydroxy-cyclopentyl)-1-{[(4-methanesulfonyl-phenyl)-acetyl]-methyl-amino}-ethyl)-phenoxy]-acetic acid A solution of Example 42 (0.83 g, 1.52 mmol) in dichloromethane (2.0 mL) was stirred with HCl in dioxane (4.0 M) (1.0 mL, 4.0 mmol) for 23 hours at room temperature under argon. The solvent was removed in vacuo, and the residue dissolved in dichloromethane (1.5 mL) and stirred with HCl in dioxane (1.5 mL, 6.0 mmol) for 46 hours. The solvent was removed in vacuo, and the residue washed with diethyl ether. The resulting solid was stirred in acetonitrile overnight, the acetonitrile was removed using a pipette, and diethyl ether was added to the acetonitrile. The solvent was removed in vacuo to give the HCl salt of the product as an off-white solid, 0.80 mmol, 52%.

$^1$H NMR (400 MHz, DMSO): δ7.86 (2H, d, J=8.4 Hz); 7.56 (2H, d, J=8.4 Hz); 7.31 (1H, t, J=8.0 Hz); 6.90–6.80 (3H, m); 6.10 (1H, d, J=7.6 Hz); 5.45 (1H, br); 4.68 (2H, s); 4.43 (1H, br); 4.16–4.06 (2H, m); 3.95–3.91 (1H, m); 3.70–3.21 (4H, m); 3.20 (3H, s); 2.83 (3H, s); 2.20 (1H, br); 1.88 (1H, br). IR (thin film) ν=3424.0, 1641.0, 1494.0. MS ($ES^+$)=491.24 $C_{24}H_{31}N_2O_7S^+$ requires 491.59.

The following compounds can be prepared by the methods given above:

[S-(R*,R*)]-{3-[1-[(Benzofuran-4-yl-acetyl)-methyl-amino]-2-(3-fluoro-pyrrolidin-1-yl)-ethyl]-phenoxy}-acetic acid,

[S-(R*,R*)]-{3-[1-[(Benzofuran-4-yl-acetyl)-methyl-amino]-2-(3-methoxy-pyrlrolidin-1-yl)-ethyl]-phenoxy}-acetic acid,

[S-(R*,R*)]-2-Benzofuran-4-yl-N-{2-(3-hydroxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-4-yl-acetyl)-methyl-amino]-2-(3-hydroxy-pyrrolidin-1-yl)-ethyl]-phenoxy}-methanesulfonic acid,

[S-(R*,R*)]-2-Benzofuran-4-yl-N-{2-(3-fluoro-pyrrolidin-1-yl)-1-[3-(2H-tetrazol-5-ylmethoxy)-phenyl]-ethyl}-N-methyl-acetamide,

[S-(R*,R*)]-2-Benzofuran-4-yl-N-{2-(3-methoxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-2-yl-acetyl)-methyl-amino]-2-(3-fluoro-pyrrolidin-1-yl)-ethyl]-phenoxy}-acetic acid,

[S-(R*,R*)]-{3-[1-[(Benzofuran-2-yl-acetyl)-methyl-amino]-2-(3-methoxy-pyrrolidin-1-yl)-ethyl]-phenoxy}-acetic acid,

[S-(R*,R*)]-2-Benzofuran-2-yl-N-{2-(3-hydroxy-pyrrolidin-1-yl)-1-[3-(2H-tetrazol-5-ylmethoxy)-phenyl]-ethyl}-N-methyl-acetamide,

[S-(R*,R*)]-2-Benzofuran-2-yl-N-{2-(3-fluoro-pyrrolidin-1-yl)-1-[3-(2H-tetrazol-5-ylmethoxy)-phenyl]-ethyl}-N-methyl-acetamide,

[S-(R*,R*)]-2-Benzofuran-2-yl-N-{2-(3-methoxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-2-yl-acetyl)-methyl-amino]-2-(3-hydroxy-pyrrolidin-1-yl)-ethyl]-phenoxy}-methanesulfonic acid, (S)-2-Benzofuran-2-yl-N-methyl-N-{2-pyrrolidin-1-yl-1-[3-(2H-tetrazol-5-ylmethoxy)-phenyl]-ethyl}-acetamide, (S)-(3-{1-[(Benzofuran-2-yl-acetyl)-methyl-amino]-2-pyrrolidin-1-yl-ethyl}-phenoxy)-methanesulfonic acid,

[S-(R*,R*)]-{3-[1-(Diphenylacetyl-methyl-amino)-2-(3-fluoro-pyrrolidin-1-yl)-ethyl]-phenoxy}-acetic acid,

[S-(R*,R*)]-{3-[1-(Diphenylacetyl-methyl-amino)-2-(3-methoxy-pyrrolidin-1-yl)-ethyl]-phenoxy}-acetic acid,

[S-(R*,R*)]-N-{2-(3-Hydroxy-pyrrolidin-1-yl)-1-[3-(2H-tetrazol-5-ylmethoxy)-phenyl]-ethyl}-N-methyl-2,2-diphenyl-acetamide,

[S-(R*,R*)]-{3-[1-(Diphenylacetyl-methyl-amino)-2-(3-hydroxy-pyrrolidin-1-yl)-ethyl]-phenoxy}-methanesulfonic acid,

[S-(R*,R*)]-N-{2-(3-Fluoro-pyrrolidin-1-yl)-1-[3-(2H-tetrazol-5-ylmethoxy)-phenyl]-ethyl}-N-methyl-2,2-diphenyl-acetamide,

[S-(R*,R*)]-N-{2-(3-Methoxy-pyrrolidin-1-yl)-1-[3-(2H-tetrazol-5-ylmethoxy)-phenyl]-ethyl}-N-methyl-2,2-diphenyl-acetamide,

[S-(R*,R*)]-[3-(2-(3-Fluoro-pyrrolidin-1-yl)-1-{[(4-methanesulfonyl-phenyl)-acetyl]-methyl-amino}-ethyl)-phenoxy]-acetic acid,

[S-(R*,R*)]-{3-[1-{[(4-Methanesulfonyl-phenyl)-acetyl]-methyl-amino}-2-(3-methoxy-pyrrolidin-1-yl)-ethyl]-phenoxy}-acetic acid,

[S-(R*,R*)]-N-{2-(3-Hydroxy-pyrrolidin-1-yl)-1-[3-(2H-tetrazol-5-ylmethoxy)-phenyl]-ethyl}-2-(4-methanesulfonyl-phenyl)-N-methyl-acetamide,

[S-(R*,R*)]-[3-(2-(3-Hydroxy-pyrrolidin-1-yl)-1-{[(4-methanesulfonyl-phenyl)-acetyl]-methyl-amino}-ethyl)-phenoxy3-methanesulfonic acid,

[S-(R*,R*)]-N-{2-(3-Fluoro-pyrrolidin-1-yl)-1-[3-(2H-tetrazol-5-ylmethoxy)-phenyl]-ethyl}-2-(4-methanesulfonyl-phenyl)-N-methyl-acetamide,

[S-(R*,R*)]-2-(4-Methanesulfonyl-phenyl)-N-{2-(3-methoxy-pyrrolidin-1-yl)-1-[3-(2H-tetrazol-5-ylmethoxy)-phenyl]-ethyl}-N-methyl-acetamide,

[S-(R*,R*)]-{3-[1-[(Benzofuran-3-yl-acetyl)-methyl-amino]-2-(3-fluoro-pyrrolidin-1-yl)-ethyl]-phenoxy}-acetic acid,

[S-(R*,R*)]-{3-[1-[(Benzofuran-3-yl-acetyl)-methyl-amino]-2-(3-methoxy-pyrrolidin-1-yl)-ethyl]-phenoxy}-acetic acid,

[S-(R*,R*)]-2-Benzofuran-3-yl-N-{2-(3-hydroxy-pyrrolidin-1-yl)-1-[3-(2H-tetrazol-5-ylmethoxy)-phenyl]-ethyl}-N -methyl -acetamide,

[S-(R*,R*)]-2-Benzofuran-3-yl-N-{2-(3-fluoro-pyrrolidin-1-yl)-1-[3-(2H-tetrazol-5-ylmethoxy)-phenyl]-ethyl}-N-methyl-acetamide,

[S-(R*,R*)]-2-Benzofuran-3-yl-N-{2-(3-methoxy-pyrrolidin-1-yl)-1-[3-(2H-tetrazol-5-ylmethoxy)-phenyl]-ethyl}-N -methyl-acetamide,

[S-(R*,R*)]-{3-[1-[(Benzofuran-3-yl-acetyl)-methyl-amino]-2-(3-hydroxy-pyrrolidin-1-yl)-ethyl]-phenoxy}-methanesulfonic acid, (S)-2-Benzofuran-3-yl-N-methyl-N-{2-pyrrolidin-1-yl-1-[3-(2H-tetrazol-5-ylmethoxy)-phenyl]-ethyl}-acetamide, and (S)-(3-{1-[(Benzofuran-3-yl-acetyl)-methyl-amino]-2-pyrrolidin-1-yl-ethyl}-phenoxy)-methanesulfonic acid.

What is claimed is:

1. A compound of Formula I or a pharmaceutically acceptable salt thereof wherein:

X=CO$_2$H or SO$_3$H;

m is an integer of from 1 to 3;

Y is hydrogen, fluoro, or OR wherein R is hydrogen or methyl;

n is an integer of from 0 to 1; and

Z is 2-benzofuranyl, 3-benzofuranyl, 4-benzofuranyl, 5-benzofuranyl, 6-benzofuranyl, 7-benzofuranyl, 2-thianaphthene, 3-thianaphthene, 4-thianaphthene, 5-thianaphthene, 6-thianaphthene, or 7-thianaphthene when n is 1.

2. A compound according to claim 1 wherein Z is 2-benzofuranyl, 3-benzofuranyl, 4-benzofuranyl, 5-benzofuranyl, 6-benzofuranyl, 7-benzofuranyl, 2-thianaphthene, 3-thianaphthene, 4-thianaphthene, 5-thianaphthene, 6-thianaphthene, or 7-thianaphthene, and n is 1.

3. A compound according to claim 1 and selected from:

(S)-(3-{1-[(Benzofuran-2-yl-acetyl)-methyl-amino]-2-pyrrolidin-1-yl-ethyl}-phenoxy)-acetic acid;

(S)-(3-{1-[(Benzofuran-3-yl-acetyl)-methyl-amino]-2-pyrrolidin-1-yl-ethyl}-phenoxy)-acetic acid;

[S-(R*,R*)]-{3-[1-[(Benzofuran-3-yl-acetyl)-methyl-amino]-2-(3-hydroxy-pyrrolidin-1-yl)-ethyl]-phenoxy}-acetic acid;

[S-(R*,R*)]-{3-[1-[(Benzofuran-2-yl-acetyl)-methyl-amino]-2-(3-hydroxy-pyrrolidin-1-yl)-ethyl]-phenoxy}-acetic acid; and

[S-(R*,R*)]-{3-[-[(Benzofuran-4-yl-acetyl)-methyl-amino]-2-(3-hydroxy-cyclopentyl)-ethyl]-phenoxy}-acetic acid.

4. A compound according to claim 1 and selected from:

(S)-(3-{(1-[(Thianaphthen-2-yl-acetyl)-methyl-amino]-2-pyrrolidin-1-yl-ethyl}-phenoxy)-acetic acid (S)-2-Benzofuran-2-yl-N-methyl-N-{2-pyrrolidin-1-yl-1-[3-(2H-tetrazol-5-ylmethoxy)-phenyl]-ethyl}-acetamide,

[S-(R*,R*)]-{3-[1-[(Benzofuran-4-yl-acetyl)-methyl-amino]-2-(3-fluoro-pyrrolidin-1-yl)-ethyl]-phenoxy}-acetic acid, (S)-(3-{1-[(Benzofuran-2-yl-acetyl)-methyl-amino]-2-pyrrolidin-1-yl-ethyl}-phenoxy)-methanesulfonic acid, and

[S-(R*,R*)]-{3-[1-[(Benzofuran-4-yl-acetyl)-methyl-amino]-2-(3-methoxy-pyrlrolidin-1-yl)-ethyl]-phenoxy}-acetic acid.

5. A pharmaceutical composition which comprises a therapeutically effective amount of a compound of claim 1 Formula I in combination with a pharmaceutically acceptable carrier in unit dosage form.

6. A method of treating arthritis which comprises administering a therapeutically effective amount of a compound according to claim 1 to a mammal in need of said treatment.

7. A method of treating pain which comprises administering a therapeutically effective amount of a compound according to claim 1 to a mammal in need of said treatment.

8. A method of treating inflammation which comprises administering a therapeutically effective amount of a compound according to claim 1 to a mammal in need of said treatment.

9. A method of treating migraine which comprises administering a therapeutically effective amount of a compound according to claim 1 to a mammal in need of said treatment.

10. A method of treating inflammatory disorders of the gastrointestinal tract which comprises administering a therapeutically effective amount of a compound according to claim 1 to a mammal in need of said treatment.

11. A method of treating irritable bowel syndrome which comprises administering a therapeutically effective amount of a compound according to claim 1 to a mammal in need of said treatment.

12. A method of treating psoriasis which comprises administering a therapeutically effective amount of a compound according to claim 1 to a mammal in need of said treatment.

13. A process for the preparation of a compound of claim 1 Formula I which comprises (a) converting an aldehyde of formula into the corresponding styrene of formula by a Wittig reaction in solvent;

(b) dihydroxylating the styrene of Step (a) above to produce a diol of formula (c) converting the diol into an expoxide;

(d) opening the epoxide with a pyrrolidine to produce an amino alcohol;

(e) transforming the amino alcohol into a diamine;

(f) coupling the diamine with an acid using a suitable coupling reagent to produce an amide;

(g) removing the benzyl protecting group by hydrogenation;

(h) esterifying the product of Step (g) above with a suitable base; and (i) converting the ester of Step (h) above into the corresponding carboxylic acid and converting to a pharmaceutically acceptable salt.

14. A compound selected from:

(S)-2-Benzofuran-2-yl-N-[1-(3-benzyloxy-phenyl)-2-pyrrolidin-1-yl-ethyl]-N-methyl-acetamide, (S)-2-Benzofuran-2-yl-N-[1-(3-hydroxy-phenyl)-2-pyrrolidin-1-yl-ethyl]-N-methyl-acetamide, (S)-2-Benzofuran-3-yl-N-[1-(3-benzyloxy-phenyl)-2-pyrrolidin-1-yl-ethyl-N-methyl-acetamide, (S)-2-Benzofuran-3-yl-N-[1-(3-hydroxy-phenyl)-2-pyrrolidin-1-yl-ethyl]-N-methyl-acetamide, (S)-(3-{1-[(Benzofuran-3-yl-acetyl)-methyl-amino]-2-pyrrolidin-1-yl-ethyl}-phenoxy)-acetic acid tert-butyl ester,

[S-(R*,R*)]-2-Benzofuran-3-yl-N-{1-(3-benzyloxy-phenyl)-2-[3-(tert-butyl-dimethyl-silanyloxy)-pyrrolidin-1-yl]-ethyl}-N-methyl-acetamide,

[S-(R*,R*)]-2-Benzofuran-3-yl-N-[2-[3-(tert-butyl-dimethyl-silanyloxy)-pyrrolidin-1-yl]-1-(3-hydroxy-phenyl)-ethyl]-N-methyl-acetamide,

[S-(R*,R*)]-(3-{1-[(Benzofuran-3-yl-acetyl)-methyl-amino]-2-[3-(tert-butyl-dimethyl-silanyloxy)-pyrrolidin-1-yl]-ethyl}-phenoxy)-acetic acid tert-butyl ester,

[S-(R*,R*)]-(3-(1-[(Benzofuran-3-yl-acetyl)-methyl-amino]-3-(3-hydroxy-pyrrolidin-1-yl)-ethyl]-phenoxy]-acetic acid tert-butyl ester,

[S-(R*,R*)]-2-Benzofuran-2-yl-N-{1-(3-benzyloxy-phenyl)-2-[3-(tert-butyl-dimethyl-silanyloxy)-pyrrolidin-1-yl]-ethyl}-N-methyl-acetamide,

[S-(R*,R*)]-2-Benzofuran-2-yl-N-[2-[3-(tert-butyl-dimethyl-silanyloxy)-pyrrolidin-1-yl]-1-(3-hydroxy-phenyl)-ethyl]-N-methyl-acetamide,

[S-(R*,R*)]-(3-{1-[(Benzofuran-2-yl-acetyl)-methyl-amino]-2-[3-(tert-butyl-dimethyl-silanyloxy)-pyrrolidin-1-yl]-ethyl}-phenoxy)-acetic acid tert-butyl ester,

[S-(R*,R*)]-{3-[1-[(Benzofuran-2-yl-acetyl)-methyl-amino]-2-(3-hydroxy-pyrrolidin-1-yl)-ethyl]-phenoxy}-acetic acid tert-butyl ester,

[S-(R*,R*)]-2-Benzofuran-4-yl-N-{1-(3-benzyloxy-phenyl)-2-[3-(tert-butyl-dimethyl-silanyloxy)-2-pyrrolidin-1-yl]-ethyl}-N-methyl-acetamide,

[S-(R*,R*)]-2-Benzofuran-4-yl-N-[2-[3-(tert-butyl-dimethyl-silanyloxy)-cyclopentyl]-1-3-hydroxy-phenyl)-ethyl]-N-methyl-acetamide,

[S-(R*,R*)]-(3-{1-[(Benzofuran-4-yl-acetyl)-methyl-amino]-2-[3-(tert-butyl-dimethyl-silanyloxy)-cyclopentyl]-ethyl}-phenoxy)-acetic acid tert-butyl ester, and

[S(R*,R*)]-{3-[1-[(Benzofuran-4-yl-acetyl)-methyl-amino]-2-(3-hydroxy-cyclopentyl)-ethyl]-phenoxy}-acetic acid tert-butyl ester.

* * * * *

UNITED STATES PATENT AND TRADEMARK OFFICE
CERTIFICATE OF CORRECTION

PATENT NO. : 6,057,357  
DATED : March 2, 2000  
INVENTOR(S) : Horwell et al.

Page 1 of 1

It is certified that error appears in the above-identified patent and that said Letters Patent is hereby corrected as shown below:

Column 44,  
Line 60, "(S) - (3-{ (1-" should read " (S) - (3-{1-".

Column 46,  
Line 55, "amino} -3-" should read "amino-}-2-".

Column 47,  
Line 8, "-cyclopentyl]-1-3-" should read "-cyclopentyl]-1 (3-".

Signed and Sealed this

Seventeenth Day of July, 2001

Attest:

Attesting Officer

NICHOLAS P. GODICI  
Acting Director of the United States Patent and Trademark Office